United States Patent
Ümit et al.

(10) Patent No.: US 11,459,582 B2
(45) Date of Patent: Oct. 4, 2022

(54) ACTIVATION OF TASTE RECEPTOR GENES IN MAMMALIAN CELLS USING CRISPR-CAS-9

(71) Applicant: B.R.A.I.N. AG, Zwingenberg (DE)

(72) Inventors: Pul Ümit, Duisburg (DE); Michael Krohn, Lorsch (DE)

(73) Assignee: B.R.A.I.N. AG, Zwingenberg (DE)

( * ) Notice: Subject to any disclaimer, the term of this patent is extended or adjusted under 35 U.S.C. 154(b) by 457 days.

(21) Appl. No.: 15/762,424

(22) PCT Filed: Sep. 23, 2016

(86) PCT No.: PCT/EP2016/072679
§ 371 (c)(1),
(2) Date: Mar. 22, 2018

(87) PCT Pub. No.: WO2017/050963
PCT Pub. Date: Mar. 30, 2017

(65) Prior Publication Data
US 2018/0273976 A1    Sep. 27, 2018

(30) Foreign Application Priority Data

Sep. 26, 2015  (EP) .................................... 15187005
Oct. 24, 2015  (EP) .................................... 15191360

(51) Int. Cl.
| | | |
|---|---|---|
| C12N 15/90 | (2006.01) | |
| C12N 15/85 | (2006.01) | |
| C12N 9/22 | (2006.01) | |
| C12N 15/113 | (2010.01) | |
| C12N 15/63 | (2006.01) | |
| C07K 14/705 | (2006.01) | |
| C12N 15/11 | (2006.01) | |
| C12N 15/62 | (2006.01) | |
| C07K 19/00 | (2006.01) | |

(52) U.S. Cl.
CPC ............ *C12N 15/85* (2013.01); *C07K 14/705* (2013.01); *C12N 9/22* (2013.01); *C12N 15/11* (2013.01); *C12N 15/1138* (2013.01); *C12N 15/63* (2013.01); *C07K 19/00* (2013.01); *C07K 2319/00* (2013.01); *C12N 15/62* (2013.01); *C12N 2310/20* (2017.05); *C12N 2310/3519* (2013.01); *C12N 2830/00* (2013.01)

(58) Field of Classification Search
CPC .................................................. C12N 2310/20
See application file for complete search history.

(56) References Cited

U.S. PATENT DOCUMENTS

2013/0210046 A1    8/2013  Krohn et al.
2014/0356959 A1   12/2014  Church et al.

FOREIGN PATENT DOCUMENTS

WO    2004069191 A2    8/2004

OTHER PUBLICATIONS

Konermann et al. (2014, Nature, vol. 517, pp. 583-588) (Year: 2014).*
Konermann et al. (ePub Oct. 12, 2014, Nature, vol. 517, pp. 583-588) (Year: 2014).*
Hochheimer et al. (Mar. 12, 2014, Chemical Senses, vol. 39, pp. 359-377). (Year: 2014).*
Supplementary Data for Konermann, two PDFs. (Year: 2014).*
Konermann et al., "Genome-scale transcriptional activation by an engineered CRISPR-Cas9 complex," Nature, 517: (2015) 583-588.
Gilbert et al.: "Genome-Scale CRISPR-Mediated Control of Gene Repression and Activation," Elsevier Inc., (2014) Cell 159, 647-661.
Shalem et al., "Genome-Scale CRISPER-Cas9 Knockout Screening in Human Cells," Science 343:84 (2014), 84-87.
Perez-Pinera et al., "RNA-guided gene activation by CRISPER-Cas9-based transcription factors"; Nature Methods, 10:10 (2013) 973-976.
Zalatan et al., "Engineering Complex Synthetic Transcriptional Programs with CRISPR RNA Scaffolds," Cell 160: (2015), 339-350.
Tanenbaum et al.; "A Protein-Tagging System for Signal Amplification in Gene Expression and Fluorescence Imaging," Cell 159: (2014) 635-646.

* cited by examiner

*Primary Examiner* — Peter Paras, Jr.
*Assistant Examiner* — David A Montanari
(74) *Attorney, Agent, or Firm* — Dilworth & Barrese, LLP

(57) ABSTRACT

Suggested is a method for enhancing the expression of taste related receptor genes encompassing the following steps: (i) providing a culture of mammalian cells, the genome of said cells comprising at least one sweet receptor domain; (ii) designing at least one type of single-guide RNA (sgRNA), the 10 to 30 nt guide sequence of said sgRNA being complementary to stretches within the non-coding and/or putative regulatory region upstream of the translation start codon of at least one sweet receptor gene; (iii) preparing a vector comprising an expression cassette encompassing at least one optionally modified CRISPR-Cas9, preferably CRISPR-dCas9VP64, and at least one optionally modified sg-RNA optionally containing aptamer structures for binding activator proteins; (iv) transfecting said culture of mammalian cells with said vector to target the genome for the presence of a DNA sequence that is complementary to the 10 to 30 nt guide sequence of said sgRNA; and (v) measuring the transcriptional enhancement of the sweet receptor mRNA by quantitative RT-PCR.

Figure 1A:
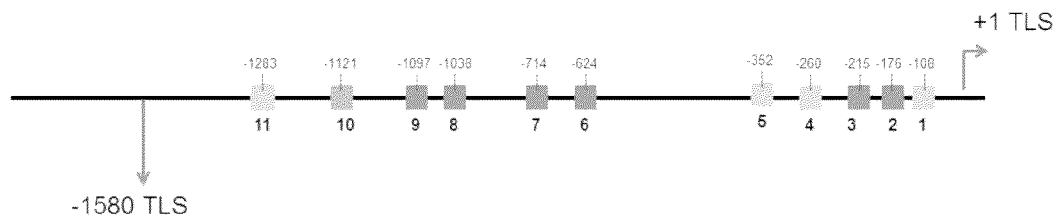
Figure 1A:
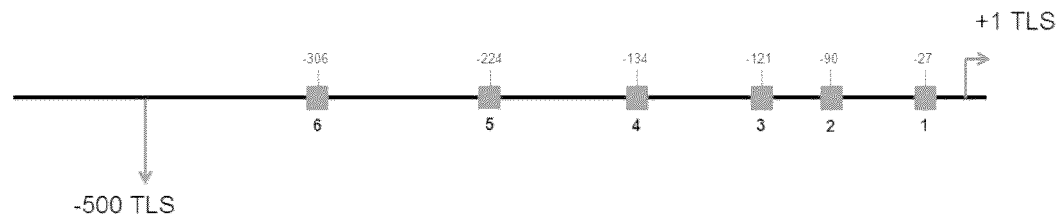
Figure 1A:
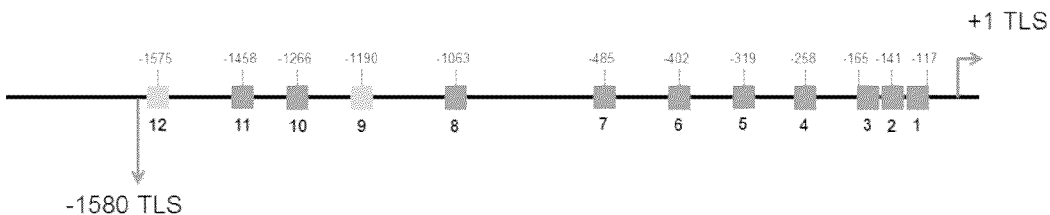
Figure 1A:
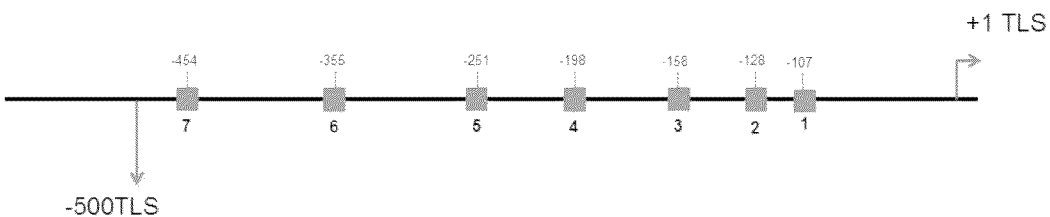
Figure 1B:
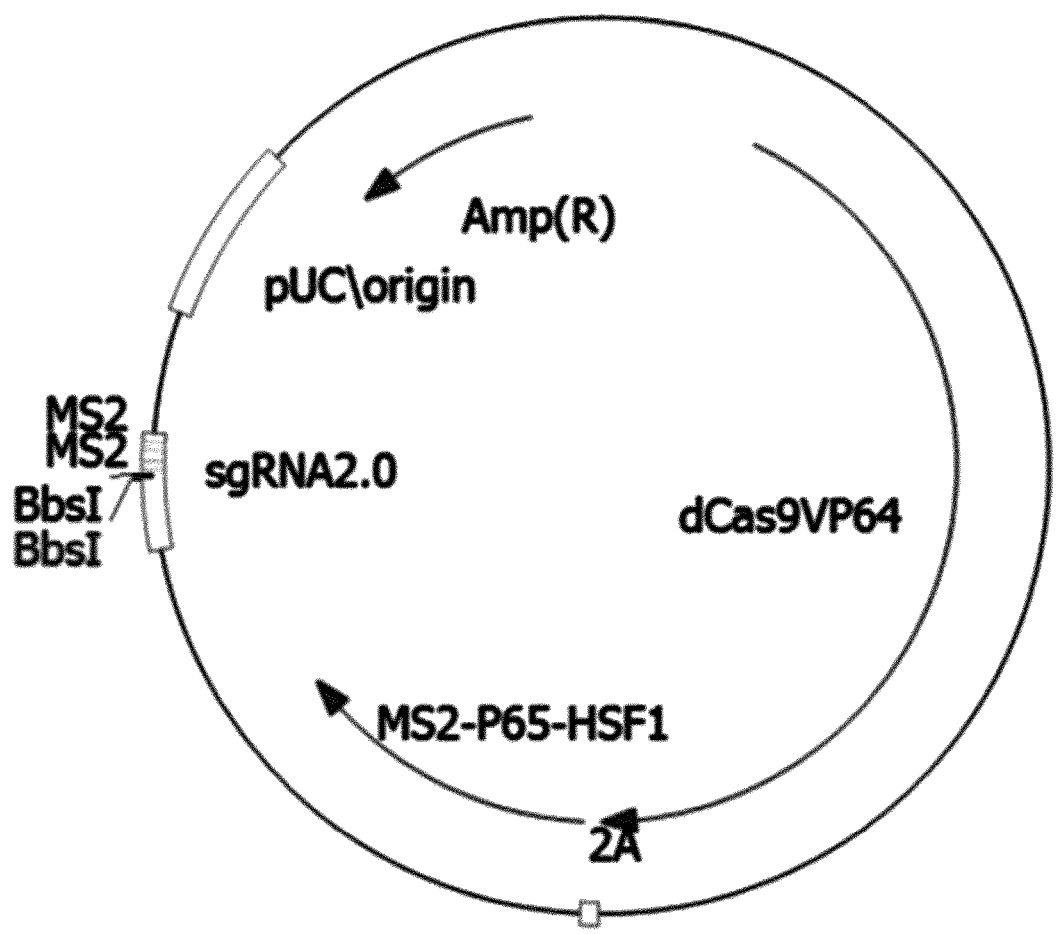
Figure 1C:

8 Claims, 6 Drawing Sheets
Specification includes a Sequence Listing.

T1R1 — positions of sgRNAs

- localisation human genome: chr1: 6555278..6579757

T1R2 — positions of sgRNAs

- localisation human genome: chr1:18839599..18859682

T1R3 — positions of sgRNAs

- localisation human genome: chr1:1266726..1269844

GNAT3 — positions of sgRNAs

- localisation human genome: chr7:80458671..80512020

ACTIVATION OF TASTE RECEPTOR GENES IN MAMMALIAN CELLS USING CRISPR-CAS-9

FIELD OF INVENTION

The present invention belongs to the area of biotechnology and refers to a new approach for activating taste receptor genes in mammalian cells using CRISPR-Cas9.

STATE OF THE ART

In times where the market for healthy food is constantly growing it is still a challenging problem finding non- or low-caloric substitutes exhibiting both similar sweetness and taste like sugar. Although it is true that state of the art counts numerous artificial sweeteners one needs taking into account that a lot of them, also those, which are already established in the market, show serious disadvantages. For example many individuals do not tolerate sorbitol. For synthetic sweeteners like Acesulfam K or aspartame doubt exists, whether they have a negative impact on health when consumed in high amounts over a long time.

The ongoing debate on obesity in developed countries and the growing health consciousness of consumers lead to an increasing demand of food and beverages with significant calorie reduction compared to products fully sweetened with carbohydrates such as sucrose, glucose, fructose or syrups such as HFCS 55 or 42. As the consumer usually is not willing to compromise on taste products should have similar sweetness intensity and taste quality as products regularly sweetened with these carbohydrates.

High intensity sweeteners are substances, which have no or virtually no calories and a sweetness potency several times higher than sugar. High intensity sweeteners or blends of high intensity sweeteners are used in food and beverages to achieve a sweet taste without adding calories to the products. Most commonly used high intensity sweeteners are not from natural origin; they were discovered accidentally and are chemically synthesized. Most of them have a widespread approval in a large number of countries. Examples are substances such as acesulfame K, alitame, aspartame, cyclamate, neohesperidine dihydrochalcone, neotame, saccharin, and sucralose. However, no high-intensity sweetener matches the taste profile of sugar completely. They differ in characteristics such as sweetness profile, side taste and off-taste characteristics. Therefore a need exists for new high-intensity sweeteners which offer either alone or in blends with existing sweeteners sweetness profiles and flavour characteristics much closer to sugar than the existing products can offer.

Besides calorie reduction many of today's consumers are seeking for food and beverage products either without artificial additives or even being fully organic. Theoretically natural high-intensity sweeteners could fulfil this demand. A number of natural high-intensity sweeteners were discovered throughout past years such as stevioside, rebaudioside, brazzein, thaumatin, mogroside, glycyrrhizin, monatin, abrusoside, monellin, phyllodulcin and others. These are substances which naturally occur in different plants and can be obtained by selective extraction measures. Besides very limited approvals and in some cases difficulties to extract products on an industrial scale none of these products can claim to offer a sugar-like taste. In fact, all of these substances show a sweetness with a far slower onset than sucrose and a very lingering sweetness. Most of these products have strong side-taste and aftertaste characteristics such as bitter, mentholic or liquorice notes or show even strong cooling or numbing sensations. Some of these products, e.g. thaumatin, can be rather regarded as being flavour enhancer than sweetener. Blending of two or more of these substances cannot overcome these taste limitations. Therefore, in the area of natural sweetener the need for new high-intensity sweeteners with a taste profile closer to sugar is even stronger than in the case of artificial sweeteners.

Major producers as for example Coca Cola have already started to develop sweeteners that can be obtained from nature. A prominent example is *stevia*, comprising stevioglycosides like Rebaudioside A, which in terms of sweetness is superior by a factor of 300 up to 450 when compared with an aqueous 0.4% b.w. solution of saccharose. Nevertheless, also *stevia* is not considered as a full alternative to sugar, since it shows an astringent and bitter aftertaste. Therefore, beverages based on *stevia*, which have recently been launched, still contain artificial sweeteners in combination with stevioglycosides.

Thus, the search for new compounds, preferably of natural origin, is still ongoing and looking into the recently published prior art shows a huge number of potential candidates, most of them however, by far too exotic to have a chance of realization. In order to evaluate the performance of a candidate as a sweetener, panel tests are conducted. 8 to 10 experienced panellists evaluate a candidate either taken alone or in a food formulation in terms of sweetness, mouth fullness, after taste and other features of a so-called sensory assay. This procedure requires a lot of time and provides results, which to a certain degree are subjective.

A biochemical approach to get results in short time with a high degree of objectivity is to prepare cell cultures expressing human sweet receptors like Tas1R2 or Tas1R3 and to stimulate a cell response by adding a candidate as an agonist. Depending on the degree of sweetness the cell answers by liberation of more or less calcium ions into the cytoplasm, which can be measured for example either by Ca-imaging or CRE-luciferase assays.

While this procedure definitely represents a smart approach, it often does not provide reliable results. The reason is that the concentration of receptors in a culture is very low and consequently the cell response is rather week. Any amplification, however, includes the risk to falsify the results.

Therefore, the problem underlying the present invention has been providing a method for enhancing the expression of receptor genes in mammalian cells for providing an improved cell based assay for the evaluation of potential sweeteners.

DESCRIPTION OF THE INVENTION

A first object of the present invention is directed to a method for enhancing the expression of taste related receptor genes encompassing the following steps:

(i) providing a culture of mammalian cells, the genome of said cells comprising at least one sweet receptor domain;

(ii) designing at least one type of single-guide RNA (sgRNA), the 10 to 30 nt guide sequence of said sgRNA being complementary to stretches within the non-coding and/or putative regulatory region upstream of the translation start codon of at least one sweet receptor gene;

(iii) preparing a vector comprising an expression cassette encompassing at least one optionally modified CRISPR-Cas9, preferably CRISPR-dCas9VP64, and at least one optionally modified sg-RNA optionally containing aptamer structures for binding activator proteins;

(iv) transfecting said culture of mammalian cells with said vector to target the genome for the presence of a DNA sequence that is complementary to the 10 to 30 nt guide sequence of said sgRNA; and (v) measuring the transcriptional enhancement of the sweet receptor mRNA by quantitative RT-PCR.

Taste receptors such as for example the sweet receptor domains Tas1R2 and Tas1R3 were targeted by CRISPR-Cas9, in particular CRISPR-dCas9VP64, in cells which normally express these receptors on a very low level which is not sufficient to measure for example a response to agonists in a cell based assay. The vectors constructed according to the present invention comprising Cas9 in general and dCas9VP64 in particular, specific sgRNA2.0 designed to target specific stretches within the non-coding region of the sweet receptor gene upstream of the start codon, and optionally containing aptamers capable for binding activator proteins and certain transcription activators led after transfection of HEK293 cells up to an 250, 300 or 50-fold increase of T1R1, T1R2 or G-protein gustducin mRNA, respectively, but only 2 to 6-fold increase of T1R3 mRNA. Activation of T1R3 mRNA, ranging from 200 to 1200-fold, was achieved by using particular combination of different T1R3-activating vectors. A functional proof of enhanced receptor expression was achieved by stimulating with saccharin after the transfection with T1R2, T1R3 and gustducin-activating vectors.

Furthermore, proliferating primary human taste cells (BR-HTC[1]) which can be used for detecting bitter tastants and modulators thereof were engineered to express sweet receptor domains Tas1R2 and TasR3 as well as the G-protein gustducin. The method according to the present invention is able to co-activate the expression of Tas1R2 and Tas1R3 by factor of up to 40 or 100 fold, respectively, by using specific combinations of sgRNA constructs.

[1] Hochheimer, A. et al., *Chem Senses.* 2014 May; 39(4):359-77. "Endogenous gustatory responses and gene expression profile of stably proliferating human taste cells isolated from fungiform papillae"

Mammalian Cells

Preferably, the mammalian cell for use in the present invention is selected from the group consisting of human cell lines: primary human taste cells (preferred; e.g. proliferating human taste cells BR-HTC), HEK293 (Human embryo kidney), Hela (Human Negroid cervix epitheloid carcinoma), MCF-7 (Human breast cancer epithelium), HaCat (human epithlium), G-361 (Human melanoma), COLO-783 (Human melanoma), Cal-33 (Human tongue epithelium), CAKI-1 (Human kidney epithlium), DU-145 (Human prostate carcinoma), HuTu (Human duodenum epithelium), HUVEC (Human umbilical vein), HBSMC-c (Human bronchial epithelium), HT29 (Human Caucasian colon adenocarcinoma grade II), A431 (human squamous carcinoma), A357 (Human skin melanoma), A549 (human lung carcinoma), IMR 32 (human caucasian neuroblastoma), IMR-90 (human lung fibroblast), NCI-H522 (human lung carcinoma), NCL-SG3 (human sweat gland), SK-MEL (Human malignant melanoma), SKOV3 (Human ovarian carcinoma), SW-480 and SW-620 (Human colon carcinoma), LnCaP (Human prostate carcinoma), LOVO (Human colon epithelium), K562 (Human Caucasian chronic myelogenous leukaemia), U937 (Human Caucasian histiocytic lymphoma), MDA-MB-231 (Human Caucasian breast adenocarcinoma), SK-N-BE(2) (Human Caucasian neuroblastoma), SH-SY5Y (Human neuroblastoma), HL60 (Human promyelocytic leukemia), Jurkat (Human leukaemic T cell lymphoblast), or eukaryotic non-human cell lines like primary taste cell lines from companion and farm animals, cat cell lines such as e.g. CRFK (Cat kidney), Fc3Tg (Cat tongue), FL74-UCD-1 (Cat lymphoblast), Fcwf-4 (Cat macrophage), or CRFK (Cat kidney); canine cell lines e.g. MDCK (Dog kidney), D-17 (Dog osteosarcoma), or A-72 (Dog fibroblast); BHK-21 (Hamster fibroblast), CHO-K1 (Hamster Chinese ovary), COS-7 (Monkey African green kidney, SV40 transformed), VERO (Monkey African green fibroblast), S49 (mouse lymphoma), Ltk (Mouse C34/An connective tissue), NG108-15 (Mouse neuroblastoma×Rat glioma hybrid), MB-49 (Mouse bladder carcinoma), B50 (Rat nervous tissue neuronal, ECACC), C6 (Rat glial tumor), BHK (Hamster Syrian kidney), Neuro-2a (Mouse Albino neuroblastoma), V79 (Hamster Chinese fibroblast), NIH/3T3 (mouse embryo fibroblast); or cell lines from the NCI-60 cell line panel (various species).

Taste Related Receptors

The term "taste related receptors" or "taste receptors", as used herein, relates to receptors embedded in the plasma membrane of taste cells that bind taste molecules including sweet, bitter, salty, sour and umami compounds as well as fatty acids. Typically, these taste receptors are either G protein-coupled receptors with several transmembrane domains or ion channels.

The binding of taste molecules leads to the activation of taste receptors, which triggers signals and signal transduction. Perception of basic taste qualities including sweet, bitter, salty, fatty, sour, umami as well as of somatosensory sensory qualities including pungency, temperature, touch, pressure, texture and other tactile stimuli are sensed and brought about by taste GPCRs (sweet, bitter, umami/amino acids, fatty acids) as well as ion channels (e.g. salty and sour taste, pungency, temperature) and molecules involved in transport of taste molecules such as e.g. fatty acid scavengers including CD36.

G-protein coupled receptors (GPCRs) represent the largest family of cell surface receptors with an estimated number of up to 1000 genes within the human genome characterized by a seven-transmembrane configuration as their main feature. (Bockaert and Pin, 1999; Pierce et al., 2002). GPCRs are activated by a multitude of different ligands, including peptides, proteins, lipids, small molecules, ions or even photons. Activated GPCRs alter their conformation allowing it to catalyze the exchange of guanosine diphosphate (GDP) for guanosine triphosphate (GTP) on the —subunit of a heterotrimeric g-protein coupled to the GPCR.

The heterodimeric GPCR T1R2/T1R3 functions as a high affinity sugar and artificial sweetener receptor. Heterodimeric co-expression of T1R2 and T1R3 in host cells results in taste receptors that respond to sweet stimuli like diverse sugars (e. g. glucose and sucrose), artificial sweetener (e. g. acesulfam K, cyclamat, saccharin) and sweet proteins like monellin, thaumatin, brazzein (Li et al., 2002; Nelson et al., 2002; Nelson et al., 2001; Zhao et al., 2002).

The cloning of T1R2 is disclosed in patent applications WO 2003 025137 A1, US 2004 0191862 A1 and US 2003 0040045 A1 The cloning of T1R3 is disclosed in patent applications WO 2003 025137 A1, WO 2003 025137 A1, US 2004 0191862 A1 and US 2003 0040045 A1. A system for the expression of said proteins in eukaryotic cells is disclosed in patent applications WO 2003 025137 A1, WO 2000 006952 A1, US 2004 0191862 A1, WO 2004 069191 A1, US 2003 0040045 A1, EP 1865316 B1, U.S. Pat. No. 8,067,235 B2 and U.S. Pat. No. 8,067,236 B2. Screening systems for putative taste modulators are disclosed e.g. in patent applications WO 2000 006952 A1, WO 2004 069191 A1, US 200 30040045 A1, EP 1865316 B1 and U.S. Pat. No. 8,067,236 B1. Yet, there is still a need for new sweet taste modulators, e.g. new artificial taste modulators such as new sweeteners utilizing such screening methods/systems.

The method of the invention can be applied for taste related receptors selected from the group consisting of transient receptor potential V1 (TRPV1), transient receptor potential A1, (TRPA1), epithelial sodium channel alpha subunit (SCNN1A), epithelial sodium channel beta subunit (SCNN1B), epithelial sodium channel gamma subunit (SCNN1G), epithelial sodium channel delta subunit (SCNN1D), transient receptor potential ML3 (TRPML3), transient receptor potential M5 (TRPM5), taste receptor, type 1, member 1 (T1R1), taste receptor, type 1, member 2 (T1R2), taste receptor, type 1, member 3 (T1R3), taste receptor, type 2, member 38 (TAS2R38), taste receptor, type 2, member 44 T(AS2R44), taste receptor, type 2, member 1 (TAS2R1), taste receptor, type 2, member 2 (TAS2R2), taste receptor, type 2, member 3 (TAS2R3), taste receptor, type 2, member 4 (TAS2R4), taste receptor, type 2, member 5 (TAS2R5), taste receptor, type 2, member 7 (TAS2R7), taste receptor, type 2, member 8 (TAS2R8), taste receptor, type 2, member 9 (TAS2R9), taste receptor, type 2, member 10 (TAS2R10), taste receptor, type 2, member 13 (TAS2R13), taste receptor, type 2, member 14 (TAS2R14), taste receptor, type 2, member 16 (TAS2R16), taste receptor, type 2, member 39 (TAS2R39), taste receptor, type 2, member 40 (TAS2R40), taste receptor, type 2, member 41 (TAS2R41), taste receptor, type 2, member 42 (TAS2R42), taste receptor, type 2, member 43 (TAS2R43), taste receptor, type 2, member 45 (TAS2R45), taste receptor, type 2, member 46 (TAS2R46), taste receptor, type 2, member 47 (TAS2R47), taste receptor, type 2, member 48 (TAS2R48), taste receptor, type 2, member 49 (TAS2R49), taste receptor, type 2, member 50 (TAS2R50), taste receptor, type 2, member 60 (TAS2R60), glutamate receptor, metabotropic 1 (mGlu1), glutamate receptor, metabotropic 4 (mGlu4), polycystic kidney disease 2-like 1, (PKD2L1), G-protein coupled receptor 120 (GPR120), G-protein coupled receptor 40 (GPR40), CD36 molecule (CD36), and potassium inwardly-rectifying channel, subfamily J, member 1 (ROMK).

In a preferred embodiment, the taste receptor is selected from the group of multimeric T1R GPCRs, more preferred from the group consisting of T1R1, T1R2 or T1R3, even more preferred the heterodimeric sweet receptor T1R2/T1R3.

In the present invention, a functional activation of the endogenous heterodimeric sweet receptor T1R2/T1R3 by specific combination of different sgRNA2.0 is demonstrated, making cloning of the genes and transfection of cells obsolete.

G-Proteins

Studies using mammalian model organisms revealed that taste related GPCRs activate heterotrimeric GTP-binding proteins after stimulation with taste molecules. For instance, bitter receptors can activate the taste-selective Gα subunit, α-gustducin (GNAT3), and the closely related α-transducin. T1R3-containing taste receptors may also activate Gα14 (Gαq). Given their similarity to the visual system, gustducin and transducin are expected to activate a phosphodiesterase (PDE) and decrease intracellular cAMP levels. Indeed, bitter stimuli were found to decrease intracellular cAMP levels in rodents. Cyclic AMP is also decreased in rodent taste tissue in response to umami stimuli. However, many studies have shown that sugars increase cAMP levels in taste tissue and the increase is not simply a secondary consequence of $Ca^{2+}$ release from intracellular stores.

In addition to the fact that GPCRs may have a preference for Gα subunits, the main binding partners of the Gα subunits appear to be Gγ13 and Gβ1 or Gβ3. Ligands binding to GPCR release the Gα subunit (Gαq, Gαi, Gαs) together with the Gβγ subunits, which subsequently interact with phospholipase PLCβ2, an isoform that is activated by Gβγ rather than the more common Gαq family subunits. Taste molecules can evoke an increased cytoplasmic $Ca^{2+}$, strong depolarization and release of the taste bud transmitters, for instance ATP using this Gαq/Gβγ/PLCβ2 signalling pathway.

It is essential that the host cell expresses a functional G-protein, preferably gustducin (e.g. GNAT3), either naturally or by means of genetic alteration of the host cell According to the present invention an endogenous G protein like gustducin or G-proteins such as G-alpha15 or G-alpha16 or other promiscuous G proteins or G protein variants, or, or another G-protein that when expressed in association with the GPCR(s) produces a functional read out may be used. In addition, G-beta and G-gamma proteins may also be used. Subvariants of G-alpha 15 and/or G-alpha 16 with modified N-termini are also well known in the art, and can be used accordingly.

In a further more preferred embodiment, the signalling molecules are selected from the non-limiting group consisting of gustducin, transient receptor potential M5 (TRPM5), phosholipase C beta 2 (PLCb2), inositoltriphosphate receptor 3 (IP3R3), phosholipase C delta 4 (PLCD4), chemokine (C—X-C motif) ligand 14 (CXCL14), adrenergic, alpha-1A-, receptor (ADRA1A), adrenergic, beta-1-, receptor (ADRB1), adenosine A2b receptor (ADORA2B), potassium voltage-gated channel subfamily C member 2 (KCNC2), potassium voltage-gated channel, KQT-like subfamily, member 1 (KCNQ1), potassium voltage-gated channel, subfamily H (eag-related), member 2 (KCNH2), guanine nucleotide binding protein (G protein), gamma 13 (GNG13), guanine nucleotide binding protein (G protein), beta polypeptide 3 (GNB3), guanine nucleotide binding protein (G protein), alpha 13 (GNA13), guanine nucleotide binding protein (G protein), alpha 11 (GNA11), guanine nucleotide binding protein (G protein), alpha 14 (GNA14), guanine nucleotide binding protein (G protein), alpha 12 (GNA12), guanine nucleotide binding protein (G protein), beta polypeptide 1 (GNB1), guanine nucleotide-binding protein G(olf) subunit alpha (GNAL), guanine nucleotide binding protein (G protein), alpha 15 (GNA15), guanine nucleotide-binding protein G(q) subunit alpha (GNAQ), pannexin 1 (PANX1), purinergic receptor P2Y, G-protein coupled, 12 (P2RY12), purinergic receptor P2X, ligand-gated ion channel, 7 (P2RX7), potassium voltage-gated channel, shaker-related subfamily, member 1 (KCNA1), potassium voltage-gated channel, shaker-related subfamily, member 2 (KCNA2), potassium voltage-gated channel, shaker-related subfamily, member 3 (KCNA3), potassium voltage-gated channel, shaker-related subfamily, member 5 (KCNA5), potassium voltage-gated channel, shaker-related subfamily, member 2 (KCNA6), potassium voltage-gated channel, Shab-related subfamily member 1 (KCNB1), potassium voltage-gated channel, Shab-related subfamily member 2 (KCNB2), potassium voltage-gated channel subfamily C member 1 (KCNC1), phosphodiesterase 1A (PDE1A), sodium channel, voltage-gated, type II, alpha subunit (SCN2A), sodium channel, voltage-gated, type III, alpha subunit (SCN3A), sodium channel, voltage-gated, type IX, alpha subunit (SCN9A), amiloride-sensitive cation channel 1 neuronal (ACCN1), amiloride-sensitive cation channel 2 neuronal (ACCN2), and amiloride-sensitive cation channel 3 neuronal (ACCN3).

CRISPR-Cas9 and Modified CRISPR-Cas9

The process according to the present invention involves a step wherein the cell culture is transfected by a vector or plasmid containing at least one catalytically inactive Cas9 (dCas9) optionally fused to activator domains, e.g. to the tetrameric repeat of the activation domain of the herpes simplex protein VP16, termed VP64 [Beerli et al., 1998; Sadowski et al., 1988], and loaded with sgRNA or in particular loaded with sgRNA2.0 recruiting one or more transcription activator factors to regulatory regions of taste related genes.

CRISPRs (clustered regularly interspaced palindromic repeats) were described in 1987 first by Japanese researchers as a series of short direct repeats interspaced with short sequences in the genome of Escherichia coli. In 2005 it was found that many spacer sequences within CRISPRs derive from plasmid and viral origins. Together with the finding that CRISPR loci are transcribed and the observation that Cas (CRISPR-associated) genes encode proteins with putative nuclease and helicase domains, it was proposed that CRISPR-Cas is an adaptive defence system that might use antisense RNAs as memory signatures of past invasions. A detailed review of the CRISPR technology and history is provided by Doudna et al. "The new frontier of genome engineering with CRISPR-Cas9" SCIENCE Vol. 364, p1077ff (2014).

According to the recent classification of the different CRISPR systems, two classes exist, which comprise 5 different CRISPR types. The RNA-guided nuclease effectors of Class 1 are multi-protein complexes, whereas Class 2 effectors act as single-component. Cas9 belongs to Class 2-type II CRISPR system and requires two RNAs, termed CRISPR RNA (crRNA) and trans-activating RNA (tracrRNA). A synthetic fusion of parts of the crRNA to parts of tracrRNA resulted in single-guide RNA (sgRNA), which can be used for the modulation of the Cas9 target site (see below). Recently, another family within the class 2 RNA-guided nuclease effectors was described, termed Cpf1 (Zetsche et al. Cell 163, 1-13, 2015). Cpf1 is a single RNA-guided endonuclease of a class 2-type V CRISPR-Cas system). It is envisioned that in another embodiment of the present invention Cas9 can be replaced by Cpf1 or other class II effectors.

In 2012 Jinek et al discovered the CRISPR-Cas9 protein being a dual-RNA-guided-DNA endonuclease using the tracrRNA:crRNA duplex to direct DNA cleavage. Cas9 uses its HNH domain for cleaving the DNA strand that is complementary to the 20-nucleotide guide sequence of the crRNA, while the RuvC-like domain of Cas9 cleaves the DNA strand opposite the complementary strand[2].

[2] Jinek et al. SCIENCE Vol. 337, p816f (2012), "A programmable dual-RNA-guided DNA endonuclease in adaptive bacterial immunity"

In addition, studies of its molecular structure obtained by electron microscopy and x-ray crystallography have shown that Cas9 undergoes large conformational rearrangements when binding to the guide RNA, with a further change upon association with a target double-stranded DNA. This change creates a channel, running between the two structural lobes of the protein that binds to the RNA-DNA hybrid as well as to the coaxially stacked dual-RNA structure of the guide corresponding to the crRNA repeat-tracrRNA anti-repeat interaction. An arginine-rich alpha helix bridges the two structural lobes of Cas9 and appears to be the hinge between them.

Single-Guide RNA and Transcription Activator Factors

The dual tracrRNA:crRNA as reported above can be engineered as a single guide RNA (sgRNA) retaining two critical features: the 20-nt sequence at the 5' end of the sgRNA determining the DNA target site by Watson-Crick base pairing, and the double-stranded structure at the 3' side of the guide sequence that binds to Cas9. This creates a simple two-component system in which changes to the guide sequence of the sgRNA can be used to program CRISPR-Cas9 to target any DNA sequence of interest as long as it is adjacent to a PAM. A modified version of sgRNA was described in which two exposed regions were replaced by MS2 aptamers known to bind phage protein MS2. In that way it is possible to recruit transcription factors to DNA-bound dCas9.[3]

[3] Parrott, A. M. et al. Nucleic Acid Res. 28(2), 489 (2000); Konermann et al, Nature, January 29, 517 (7536), 583-8 (2015)"Genome-scale transcriptional activation by an engineered CRISPR-Cas9 complex"

Expression Cassette

The expression cassette comprises one eukaryotic promoter for the transcription of dCas9, optionally fused to activator domains, e.g. VP64, a second eukaryotic promoter for the transcription of MS2-P65-HSTF1 and a third eukaryotic promoter (RNA polymerase III-dependent) for transcription of the sgRNA2.0. P65 (human nFκB transcription factor) and HSTF1 (human heat shock transcription factor 1) are transcription factors which are brought to the site of desired transcription by the help of the MS2-binding RNA-aptamer and expression of MS2-P65-HSTF1 fusion protein. Optionally the expression of MS2-P65-HSTF1 is coupled to the expression of Cas9 by e.g. a 2A linker or IRES site for co-expression of Cas9 and MS2-P65-HSTF1. The 2A linker comprises about 20 amino acids and is derived from the picornavirus FMDV (Ryan et al., 1991 J Gen Virol; Szymczak and Vignali, 2005 Expert Opin Biol Ther). The sgRNA2.0 sequence, comprising sgRNA with 2 MS2-binding aptamers corresponds to the sequence published by Konermann et al. (2015). Insertion of new guide sequences occurs by cleavage of the vector with the type IIS restriction enzyme BbsI and ligation of double-stranded DNA. The latter is generated by hybridization of two complementary oligonucleotides containing the guide sequence and the BbsI overhangs. A one-step restriction-ligation protocol has been established allowing rapid insertion of guide sequences into the plasmid vector. To screen for activating guide sequences, 11 constructs for T1R1, 6 constructs for T1R2, 12 constructs for T1R3 and 7 constructs for GNAT3 activation were created and tested for their ability to activate the transcription of the respective target genes.

Determination of Transcriptional Enhancement

For the quantitative determination of the mRNA level in cells transfected with the pBbsI-dCas9VP64-SAM plasmid variants qRT-PCRs (quantitative reverse transcription PCRs) were performed. In brief, 160,000 cells were seeded per cavity of a 24 well plate in 500 µL DMEM-medium containing 10% FCS and 4 mM L-glutamin. Cells were counted via Casy-Cell-Counter.

After incubation of the cells for 24 h at 37° C. and 5% $CO_2$, the cells were transfected with a mixture of the four plasmid DNAs (500 ng DNA in total), 125 µL Opti-MEM medium and 2.5 µL Lipofectamin 2000.

After transfection cells were further incubated for 48 h at 37° C. and 5% $CO_2$. For preparation of total RNA the medium was removed, cells washed once with PBS and for total RNA-isolation the "NucleoSpin RNA" kit was used according to manufactures manual (Macherey & Nagel, Braunschweig Germany). 1 µg of each total RNA was applied for cDNA synthesis using "ProtoScript® II First Strand cDNA Synthesis Kit" (NEB, E6560L).

For qRT-PCR we used 2 µL of each cDNA diluted in 5.7 µL of Baker $H_2O$. A dilution series from 1:1 to 1:16 in two steps was prepared. qRT-PCR was performed in duplicate. As a "no template control" we used 5.7 µL Baker H$_2$O. Then 1.8 µL of the specific primer mixture (different primer composition for the different targets) and 7.5 µL "SsoFast™ EvaGreen^® Supermix" (BioRad, 1725200) were added.

For qRT-PCR a *CFX Connect™ Real-Time PCR Detection System BioRad,*1855200) was used. As internal control we used primer specific for Topoisomerase1 mRNA.

Screening Assay

Another object of the present invention is related to a screening assay using the method as described above for identifying novel taste modulators. More particularly, said assay encompasses measuring cell response to taste molecules by Fluo-4 fluorescent calcium imaging assay. It was found, that a response of the cells according to the invention to taste molecules leads to an increase in intracellular calcium, which was measured by the Fluo-4 fluorescent calcium imaging assay. Briefly, human taste cells were seeded in 96-well plates and stained with Fluo4-AM. Changes in Ca$^{2+}$-dependent Fluo-4 fluorescence were recorded on a Molecular Devices fluorescence microplate reader. Measurement was started by addition of increasing concentrations of the taste molecules. Addition of saccharin at different concentrations led to an increase of Fluo4-fluorescence in vector-treated HEK293 cells as compared to wild-type HEK293 cells. Calcium signals for each test molecule are depicted as relative fluorescence units (RFU).

SHORT DESCRIPTION OF THE FIGURES

FIG. 1A: Target location of the sgRNA-sequences in the non-coding upstream region of the indicated genes. 1B: Vector map comprising cas9 cassette; 1C: structure of sgRNA2.0 sequence (U6: human RNA polymerase III promoter sequence; S: spacer sequence from non-coding upstream region of the respective human T1R gene: MS2: RNA aptamer sequence)

Figure 2A:
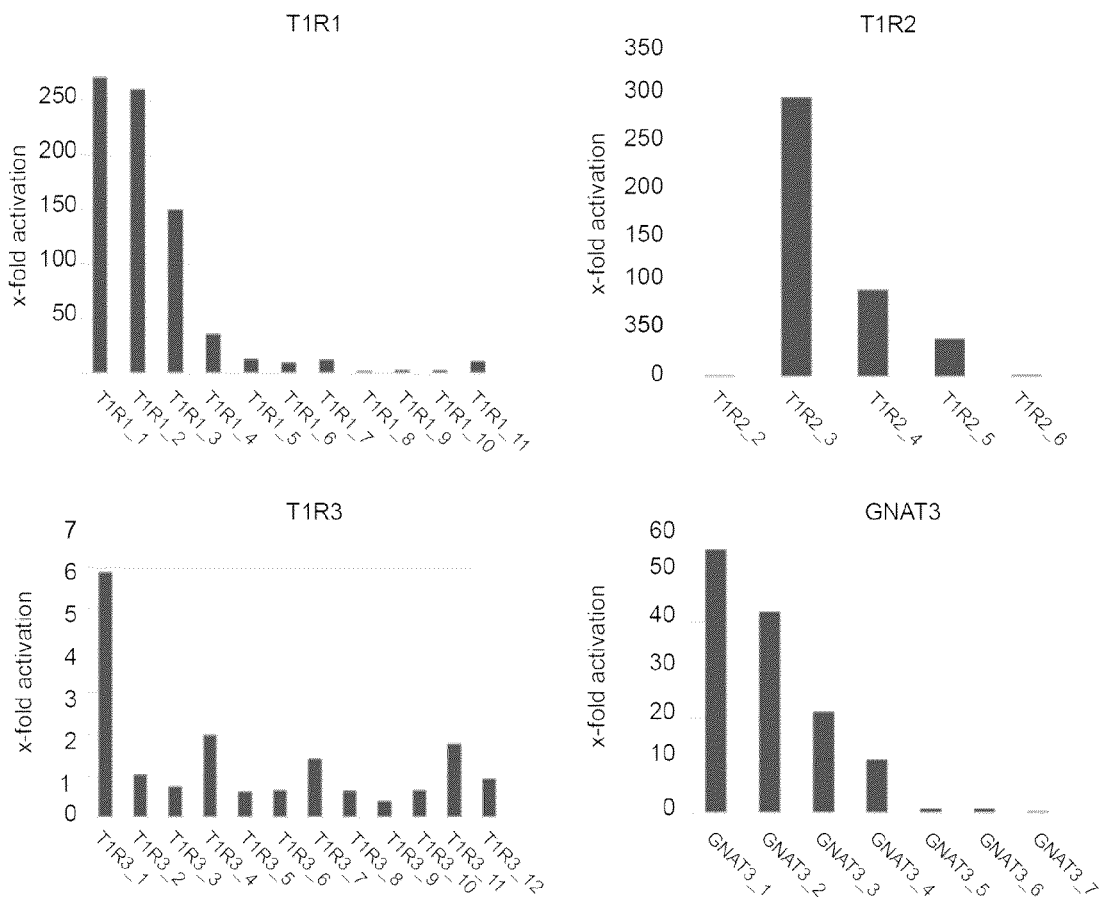

FIG. 2A: Fold change of mRNA expression of the indicated genes compared to wild type/with vectors comprising indicated sgRNAs. 2B: Fold change of mRNA expression of the T1R3 gene compared to wild type/with vectors comprising different sgRNAs. The clusters have the following meaning (numbers refer to FIG. 1A): Cluster 6: sgRNA2.0t1r3_1, _5, _7, _8; Cluster 1: sgRNA2.0t1r3_1, _3, _4, _5; Cluster 5: sgRNA2.0t1r3_3, _4, _6, _7; Cluster 2: sgRNA2.0t1r3_4, _5, _6, _7

Figure 3:
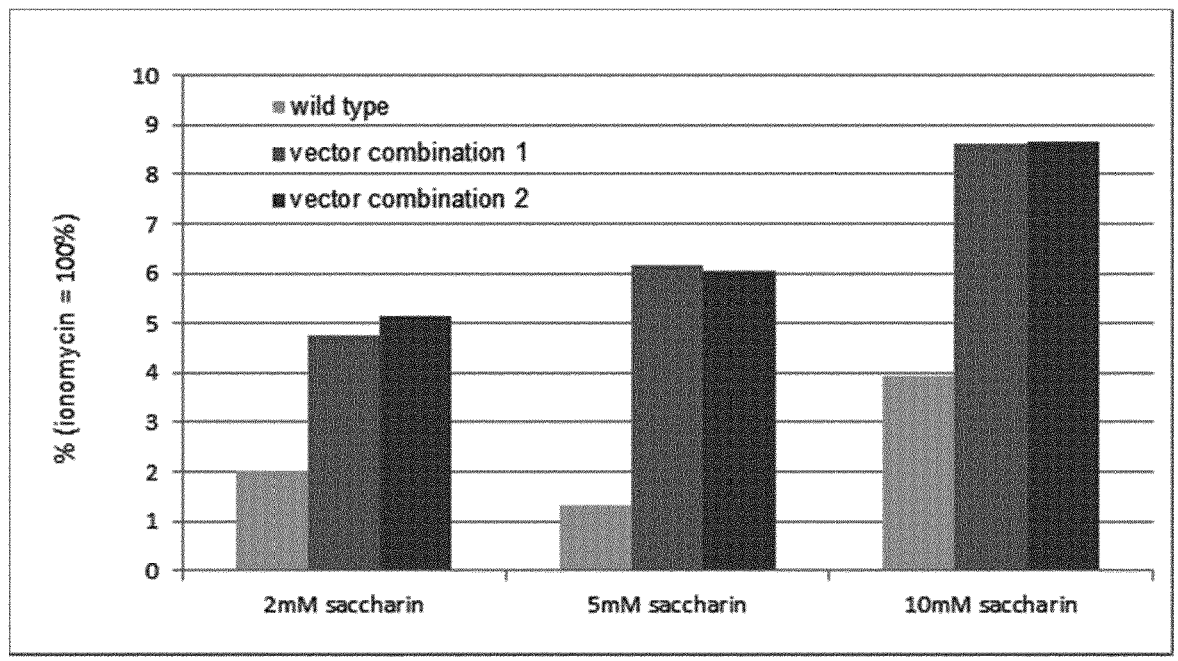

FIG. 3: Stimulation with saccharin and receptor-specific response in cells transfected with different sgRNA clusters (as explained in example 3). In wild type cells the T1R2/T1R3 genes are hardly active and therefore the heterodimeric sweet receptor is expressed on a very low level.

Figure 4A:
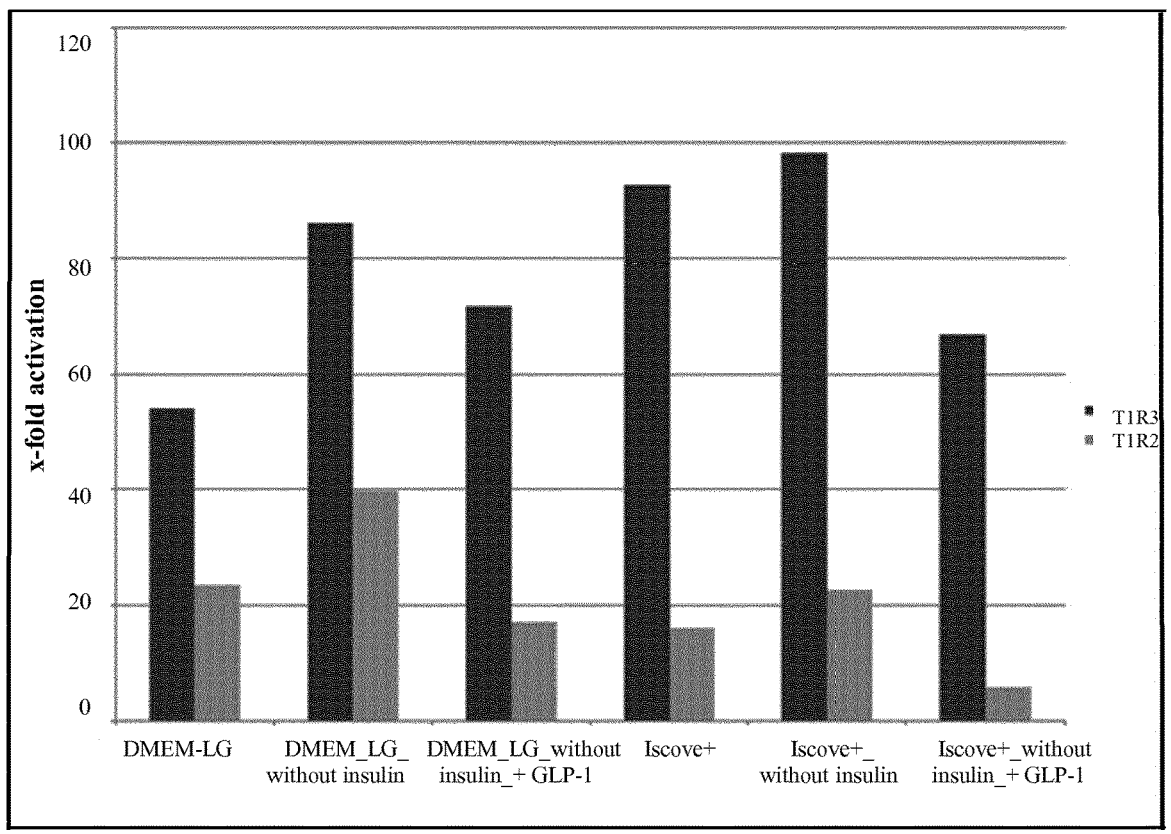

FIG. 4A: Fold change of mRNA expression of the Tas1R2 and Tas1R3 genes in HTC cultivated in different media (as indicated) after transduction with adenoviral vectors expressing dCas9VP64, MS2-p65-HSF1 and four different sgRNA2.0 with specific combination of guide sequences in tandem orientation: gnat3_1, t1r3_4, t1r3_6, t1r2_3 (tandem_sweet). The fold change was normalized against the expression level of the target genes in HTC transduced with dCas9VP64, MS2-p65-HSF1 and empty sgRNA2.0 control adenoviral vectors. 4B: 10 µl aliquots of qRT-PCR reactions performed with total RNA prepared from HTC transduced with adenoviral vectors expressing CRISPR-dCas9, VP64, sgRNA2.0, MS2, p65 and HSF1 and either tandem_sweet (expressing the four sgRNA2.0 as in 4A) or empty sgRNA2.0 control (without specific guide sequences), respectively, were separated on 1% agarose gel. The T1R3 and TOP1 amplicons are indicated.

EXAMPLES

Example 1

Transcriptional activation of T1R1-, T1R2-, T1R3- and α-gustducin (GNAT3)-mRNA by transfection of HEK293 cells with a vector comprising an expression cassette consisting of CRISPR-dCas9, VP64, sgRNA2.0, MS2, p65 and HSF1. 7 to 12 different species of sgRNAs were designed to target specific stretches of the non-coding region of the T1R1, T1R2, T1R3 or α-gustducin (GNAT3) gene, respectively. FIG. 1A shows the target location of the sgRNA-sequences in the non-coding upstream region of the indicated genes.

Figure 2B:
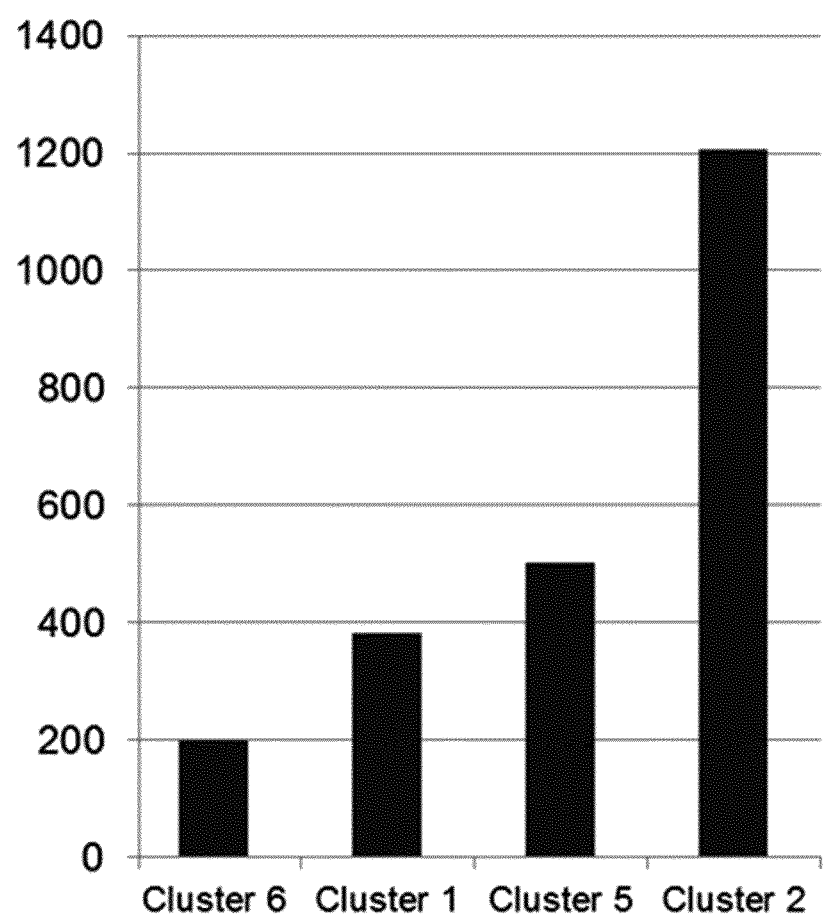

Transcriptional enhancement was quantified by quantitative RT-PCR as shown in FIG. 2A. Provided is the fold change of mRNA expression of indicated genes compared with vectors comprising different sgRNAs relative to wild type cells transfected with vectors without specific guide sequences. Depending on the binding site of the activators up to 250, 300 or 50-fold increase of T1R1, T1R2 or G-protein gustducin mRNA, respectively, could be achieved. In contrast, no significant transcriptional enhancement of the T1R3-mRNA was observed with any of the 12 T1R3-constructs. However, transcript level enhancement of the T1R3-mRNA, ranging from 200 to 1200-fold, was obtained by co-transfection of the cells with 4 different T1R3-specific vectors (FIG. 2B). The clusters have the following meaning (numbers refer to FIG. 1A):
Cluster 6: sgRNA2.0-T1R3_1, _5, _7, _8
Cluster 1: sgRNA2.0-T1R3_1, _3, _4, _5
Cluster 5: sgRNA2.0-T1R3_3, _4, _6, _7
Cluster 2: sgRNA2.0-T1R3_4, _5, _6, _7

Example 2

Functional assay for the heterodimeric sweet receptor T1R2/T1R3 in HEK293 cells transfected with different vectors comprising dCas9-VP64, MS2-p65-HSF1, sgRNA2.0 specific for T1R2, T1R3, and gustducin alpha (GNAT3). Ionomycin was used as -unspecific-positive control for receptor activity in the Fluo-4 assay monitoring intracellular calcium concentration. Response to ionomycin was set as 100%. Stimulation with saccharin shows a clear receptor-specific response in cells transfected with sgRNA clusters, whereas in the wild type cells the T1R2/TR3 genes are hardly active and therefore the heterodimeric sweet receptor is expressed on a very low level (FIG. 3).
Vector combination 1: 4×cas9, 4×sgRNA2.0 (GNAT3_1, T1R2_3, T1R3_4, T1R3_6)
Vector combination 2: 4×cas9, 4×sgRNA2.0 (GNAT3_2, T1R2_4, T1R3_5, T1R3_6)

Example 3

Figure 4B:
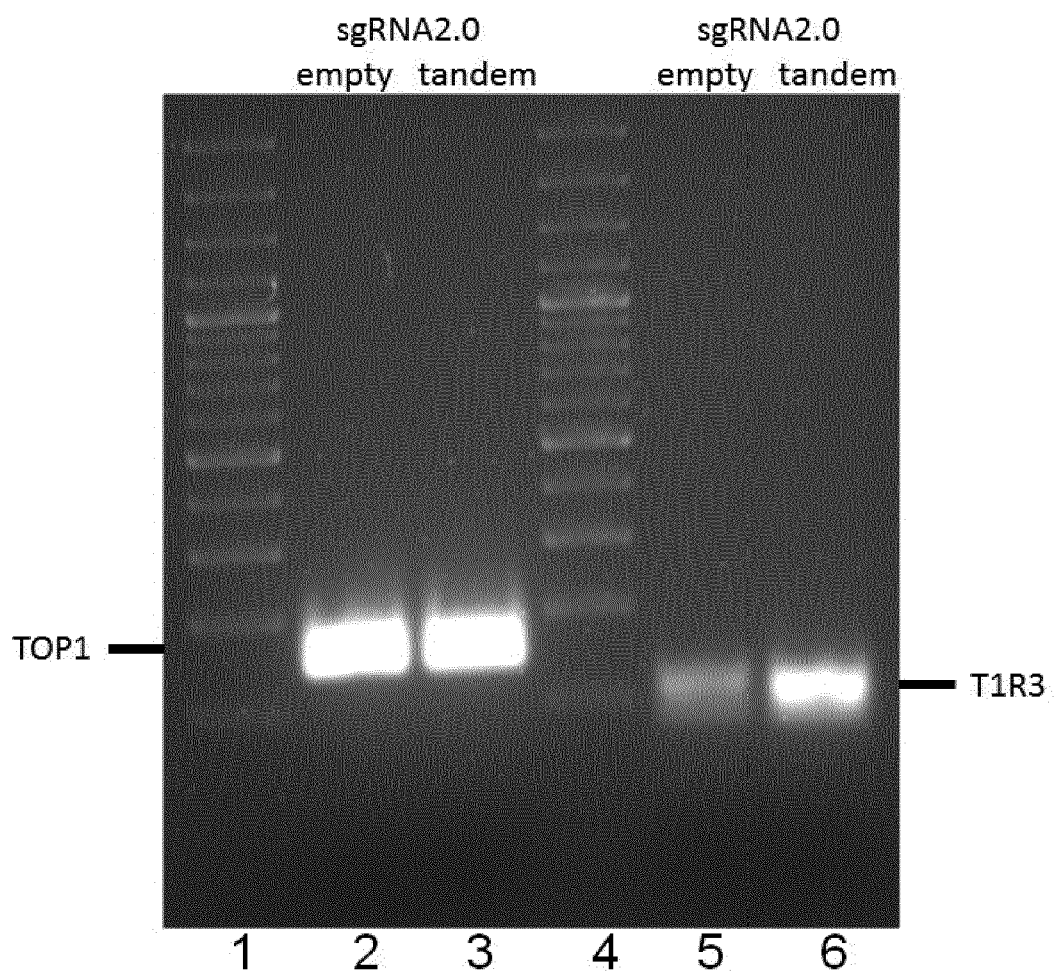

Quantitative RT-PCR with human primary taste cells BR-HTC (WO2013/160415). Transcriptional enhancement was quantified by quantitative RT-PCR as shown in FIG. 4A. Provided is the fold change of mRNA expression of T1R2 and T1R3 genes in HTC by transduction with adenoviral vectors expressing dCas9-VP64, MS2-p65-HSF1 and sgRNA2.0 with four different guide sequences targeting upstream regions of gnat-3, T1R2 and T1R3 promoters, respectively (U6-sgRNA2.0-gnat3_1, U6-sgRNA2.0- t1r3_4, U6-sgRNA2.0-t1r3_6, U6-sgRNA2.041r2_3). The mRNA level of HTC transduced with adenoviral vectors expressing dCas9-VP64, MS2-p65-HSF1 and empty sgRNA2.0 was defined as 1. Depending on the cultivation media (indicated in the FIG. 4A) up to 40 or 100-fold increase of T1R2 or T1R3 mRNA, respectively, could be achieved. Aliquots of the four qRT-PCR reactions were analysed by agarose gel electrophoresis (FIG. 4B). Consistent with the qRT-PCR data, the transcriptional enhancement of T1R3 in HTC transduced with dCas9-VP64, MS2-p65-HSF1 and tandem adenoviral vector (lane 5) could be detected compared to empty sgRNA2.0 vector control (compare lanes 5 and 6). In contrast, the expression level of the internal control gene TOP1 was not affected by adenoviral transduction (lanes 2 and 3). Thus, the designed sgRNA2.0 constructs and the method provided here, allows the simultaneous modulation of taste related genes in human taste cells.

The invention claimed is:

1. A method for enhancing the expression of taste related receptor genes comprising:

(i) providing a culture of mammalian cells, the genome of said cells comprising at least one sweet receptor domain selected from T1R1, T1R2, T1R3 or at least one domain of G-protein a-gustducin (GNAT3), (ii) designing at least one type of single-guide RNA (sgRNA), the 10 to 30 nt guide sequence of said sgRNA being complementary to stretches within the non-coding and/or putative regulatory region upstream of the translation start codon of at least one sweet receptor gene, (iii) preparing a vector comprising an expression cassette comprising at least one nucleic acid encoding CRISPR-dCas9VP64, and at least one sgRNA from step (ii), optionally containing aptamer structures for binding activator proteins, (iv) transfecting said culture of mammalian cells with said vector to target the genome for the presence of a DNA sequence that is complementary to the 10 to 30 nt guide sequence of said sgRNA; and (v) measuring the transcriptional enhancement of the sweet receptor mRNA by quantitative RT-PCR, wherein the sgRNA of the step (ii) is selected from:
(a) sgRNA2.0-t1r1_1 to sgRNA2.0-t1r1_11,
(b) sgRNA2.0-t1r2_3 to sgRNA2.0-t1r2_6,
(c) Cluster 6: sgRNA2.0t1r3_1, _5, _7, _8, Cluster 1: sgRNA2.0-t1r3_1, _3, _4, _5, Cluster 5: sgRNA2.0-t1r3_3, _4, _6, _7 or Cluster 2: sgRNA2.0-t1r3_4, _5, _6, _7, and
(d) sgRNA2.0-gnat3_1 to sgRNA2.0-gnat3_7, and wherein the transcriptional enhancement of the sweet receptor mRNA is at least 50-fold higher than baseline levels.

2. The method of claim 1, wherein the mammalian cells are primary human taste cells.

3. The method of claim 1, wherein the sgRNA is a sgRNA2.0 with a targeting sequence on the 5'-end and one or several aptamers for recruiting transcription activator factors.

4. The method of claim 3, wherein said sgRNA2.0 recruits at least one transcription activator factor.

5. The method of claim 4, wherein said transcription activator factors encompass p65 and/or HSF1.

6. The method of claim 1, wherein said vector comprises an expression cassette additionally comprising VP64, MS, p65 and/or HSF-1.

7. The method of claim 3, wherein said aptamers are MS2 aptamers.

8. The method of claim 1, wherein said at least one sweet receptor domain is selected from T1R2 or T1R3.

* * * * *

SEQUENCE LISTING

```
<160> NUMBER OF SEQ ID NOS: 39

<210> SEQ ID NO 1
<211> LENGTH: 6598
<212> TYPE: PRT
<213> ORGANISM: streptococcus pyogenes

<400> SEQUENCE: 1

Gly Thr Thr Gly Ala Cys Ala Thr Thr Gly Ala Thr Thr Ala Thr Thr
1               5                   10                  15

Gly Ala Cys Thr Ala Gly Thr Thr Ala Thr Thr Ala Ala Thr Ala Gly
                20                  25                  30

Thr Ala Ala Thr Cys Ala Ala Thr Thr Ala Cys Gly Gly Gly Gly Thr
                35                  40                  45

Cys Ala Thr Thr Ala Gly Thr Thr Cys Ala Thr Ala Gly Cys Cys Cys
            50                  55                  60

Ala Thr Ala Thr Ala Thr Gly Gly Ala Gly Thr Thr Cys Cys Gly Cys
65                  70                  75                  80

Gly Thr Thr Ala Cys Ala Thr Ala Ala Cys Thr Thr Ala Cys Gly Gly
                85                  90                  95

Thr Ala Ala Ala Thr Gly Gly Cys Cys Cys Gly Cys Cys Thr Gly Gly
                100                 105                 110

Cys Thr Gly Ala Cys Cys Gly Cys Cys Cys Ala Ala Cys Gly Ala Cys
            115                 120                 125

Cys Cys Cys Cys Gly Cys Cys Cys Ala Thr Thr Gly Ala Cys Gly Thr
130                 135                 140

Cys Ala Ala Thr Ala Ala Thr Gly Ala Cys Gly Thr Ala Thr Gly Thr
145                 150                 155                 160

Thr Cys Cys Cys Ala Thr Ala Gly Thr Ala Ala Cys Gly Cys Cys Ala
                165                 170                 175

Ala Thr Ala Gly Gly Gly Ala Cys Thr Thr Thr Cys Cys Ala Thr Thr
                180                 185                 190

Gly Ala Cys Gly Thr Cys Ala Ala Thr Gly Gly Gly Thr Gly Gly Ala
            195                 200                 205

Gly Thr Ala Thr Thr Thr Ala Cys Gly Gly Thr Ala Ala Ala Cys Thr
        210                 215                 220

Gly Cys Cys Cys Ala Cys Thr Thr Gly Gly Cys Ala Gly Thr Ala Cys
225                 230                 235                 240

Ala Thr Cys Ala Ala Gly Thr Gly Thr Ala Thr Cys Ala Thr Ala Thr
                245                 250                 255

Gly Cys Cys Ala Ala Gly Thr Ala Cys Gly Cys Cys Cys Cys Cys Thr
            260                 265                 270

Ala Thr Thr Gly Ala Cys Gly Thr Cys Ala Ala Thr Gly Ala Cys Gly
                275                 280                 285

Gly Thr Ala Ala Ala Thr Gly Gly Cys Cys Cys Gly Cys Cys Thr Gly
            290                 295                 300
```

-continued

```
Gly Cys Ala Thr Thr Ala Thr Gly Cys Cys Cys Ala Gly Thr Ala Cys
305                 310                 315                 320

Ala Thr Gly Ala Cys Cys Thr Thr Ala Thr Gly Gly Gly Ala Cys Thr
                325                 330                 335

Thr Thr Cys Cys Thr Ala Cys Thr Thr Gly Gly Cys Ala Gly Thr Ala
            340                 345                 350

Cys Ala Thr Cys Thr Ala Cys Gly Thr Ala Thr Thr Ala Gly Thr Cys
        355                 360                 365

Ala Thr Cys Gly Cys Thr Ala Thr Thr Ala Cys Cys Ala Thr Gly Gly
    370                 375                 380

Thr Gly Ala Thr Gly Cys Gly Gly Thr Thr Thr Thr Gly Gly Cys Ala
385                 390                 395                 400

Gly Thr Ala Cys Ala Thr Cys Ala Ala Thr Gly Gly Gly Cys Gly Thr
                405                 410                 415

Gly Gly Ala Thr Ala Gly Cys Gly Gly Thr Thr Thr Gly Ala Cys Thr
            420                 425                 430

Cys Ala Cys Gly Gly Gly Gly Ala Thr Thr Thr Cys Cys Ala Ala Gly
        435                 440                 445

Thr Cys Thr Cys Cys Ala Cys Cys Cys Cys Ala Thr Thr Gly Ala Cys
    450                 455                 460

Gly Thr Cys Ala Ala Thr Gly Gly Gly Ala Gly Thr Thr Thr Gly Thr
465                 470                 475                 480

Thr Thr Thr Gly Gly Cys Ala Cys Cys Ala Ala Ala Ala Thr Cys Ala
                485                 490                 495

Ala Cys Gly Gly Gly Ala Cys Thr Thr Thr Cys Cys Ala Ala Ala Ala
            500                 505                 510

Thr Gly Thr Cys Gly Thr Ala Ala Cys Ala Ala Cys Thr Cys Cys Gly
        515                 520                 525

Cys Cys Cys Cys Ala Thr Thr Gly Ala Cys Gly Cys Ala Ala Ala Thr
    530                 535                 540

Gly Gly Gly Cys Gly Gly Thr Ala Gly Gly Cys Gly Thr Gly Thr Ala
545                 550                 555                 560

Cys Gly Gly Thr Gly Gly Gly Ala Gly Gly Thr Cys Thr Ala Thr Ala
                565                 570                 575

Thr Ala Ala Gly Cys Ala Gly Ala Gly Cys Thr Cys Gly Thr Thr Thr
            580                 585                 590

Ala Gly Thr Gly Ala Ala Cys Cys Gly Thr Cys Ala Gly Ala Thr Cys
        595                 600                 605

Gly Cys Cys Thr Gly Gly Ala Gly Ala Cys Gly Cys Cys Ala Thr Cys
    610                 615                 620

Cys Ala Cys Gly Cys Thr Gly Thr Thr Thr Thr Gly Ala Cys Cys Thr
625                 630                 635                 640

Cys Cys Ala Thr Ala Gly Ala Cys Cys Gly Gly Gly Ala Cys Cys Gly
                645                 650                 655

Ala Thr Cys Cys Ala Gly Cys Cys Thr Cys Cys Gly Gly Ala Gly Cys
            660                 665                 670

Gly Gly Cys Cys Gly Cys Cys Ala Cys Cys Ala Thr Gly Gly Gly Cys
        675                 680                 685

Ala Ala Gly Cys Cys Cys Ala Thr Cys Cys Cys Thr Ala Ala Cys Cys
    690                 695                 700

Cys Cys Cys Thr Gly Thr Thr Gly Gly Gly Cys Thr Gly Gly Ala
705                 710                 715                 720

Cys Ala Gly Cys Ala Cys Cys Gly Cys Thr Cys Cys Cys Ala Ala Ala
```

-continued

```
                725                 730                 735
Ala Ala Gly Ala Ala Ala Gly Gly Ala Ala Gly Gly Thr Gly Gly
                740                 745                 750
Gly Cys Ala Thr Thr Cys Ala Cys Gly Gly Cys Gly Thr Gly Cys Cys
                755                 760                 765
Thr Gly Cys Gly Gly Cys Cys Gly Ala Cys Ala Ala Ala Ala Gly
                770                 775                 780
Thr Ala Cys Ala Gly Cys Ala Thr Cys Gly Gly Cys Cys Thr Gly
785                 790                 795                 800
Cys Thr Ala Thr Cys Gly Gly Cys Ala Cys Cys Ala Ala Thr Ala Gly
                805                 810                 815
Cys Gly Thr Gly Gly Gly Cys Thr Gly Gly Gly Cys Cys Gly Thr Thr
                820                 825                 830
Ala Thr Cys Ala Cys Ala Gly Ala Cys Gly Ala Ala Thr Ala Cys Ala
                835                 840                 845
Ala Gly Gly Thr Ala Cys Cys Cys Ala Gly Cys Ala Ala Gly Ala Ala
                850                 855                 860
Gly Thr Thr Cys Ala Ala Gly Thr Gly Cys Thr Gly Gly Gly
865                 870                 875                 880
Ala Ala Thr Ala Cys Ala Gly Ala Cys Ala Gly Gly Cys Ala Cys Thr
                885                 890                 895
Cys Thr Ala Thr Cys Ala Ala Gly Ala Ala Ala Ala Ala Cys Cys Thr
                900                 905                 910
Thr Ala Thr Cys Gly Gly Gly Gly Cys Thr Cys Thr Gly Cys Thr Gly
                915                 920                 925
Thr Thr Thr Gly Ala Cys Thr Cys Ala Gly Gly Cys Gly Ala Gly Ala
                930                 935                 940
Cys Cys Gly Cys Cys Gly Ala Gly Gly Cys Cys Ala Cys Cys Ala Gly
945                 950                 955                 960
Gly Thr Thr Gly Ala Ala Gly Ala Gly Gly Ala Cys Cys Gly Cys Ala
                965                 970                 975
Ala Gly Gly Cys Gly Ala Ala Gly Gly Thr Ala Cys Ala Cys Cys Cys
                980                 985                 990
Gly Gly Ala Gly Gly Ala Ala Gly Ala Ala Cys Ala Gly Gly Ala Thr
                995                 1000                1005
Cys Thr Gly Cys Thr Ala Thr Cys Thr Gly Cys Ala Gly Gly Ala Gly
                1010                1015                1020
Ala Thr Cys Thr Thr Cys Ala Gly Cys Ala Ala Cys Gly Ala Gly Ala
1025                1030                1035                1040
Thr Gly Gly Cys Cys Ala Ala Gly Gly Thr Gly Gly Ala Cys Gly Ala
                1045                1050                1055
Cys Ala Gly Cys Thr Thr Cys Thr Thr Cys Cys Ala Cys Ala Gly Gly
                1060                1065                1070
Cys Thr Gly Gly Ala Gly Gly Ala Gly Ala Cys Thr Thr Cys Cys
                1075                1080                1085
Thr Thr Gly Thr Cys Gly Ala Gly Gly Ala Gly Gly Ala Thr Ala Ala
                1090                1095                1100
Gly Ala Ala Gly Cys Ala Cys Gly Ala Ala Cys Gly Ala Cys Ala Cys
1105                1110                1115                1120
Cys Cys Cys Ala Thr Cys Thr Thr Cys Gly Gly Cys Ala Ala Cys Ala
                1125                1130                1135
Thr Ala Gly Thr Cys Gly Ala Cys Gly Ala Gly Gly Thr Cys Gly Cys
                1140                1145                1150
```

-continued

```
Thr Thr Ala Thr Cys Ala Cys Gly Ala Gly Ala Ala Gly Thr Ala Cys
        1155                1160                1165

Cys Cys Cys Ala Cys Cys Ala Thr Cys Thr Ala Cys Cys Ala Cys Cys
    1170                1175                1180

Thr Gly Cys Gly Ala Ala Ala Gly Ala Ala Ala Thr Thr Gly Gly Thr
1185                1190                1195                1200

Gly Gly Ala Thr Ala Gly Cys Ala Cys Cys Gly Ala Thr Ala Ala Ala
                1205                1210                1215

Gly Cys Cys Gly Ala Cys Thr Thr Gly Cys Gly Ala Cys Thr Thr Ala
            1220                1225                1230

Thr Cys Thr Ala Cys Thr Thr Gly Gly Cys Thr Cys Thr Gly Gly Cys
        1235                1240                1245

Gly Cys Ala Cys Ala Thr Gly Ala Thr Thr Ala Ala Gly Thr Thr Cys
    1250                1255                1260

Ala Gly Gly Gly Gly Cys Cys Ala Cys Thr Thr Cys Cys Thr Gly Ala
1265                1270                1275                1280

Thr Cys Gly Ala Gly Gly Gly Cys Gly Ala Cys Cys Thr Thr Ala Ala
                1285                1290                1295

Cys Cys Cys Cys Gly Ala Cys Ala Ala Cys Ala Gly Thr Gly Ala Cys
            1300                1305                1310

Gly Thr Ala Gly Ala Cys Ala Ala Ala Thr Thr Gly Thr Thr Cys Ala
        1315                1320                1325

Thr Cys Cys Ala Gly Cys Thr Thr Gly Thr Ala Cys Ala Gly Ala Cys
    1330                1335                1340

Cys Thr Ala Thr Ala Ala Cys Cys Ala Gly Cys Thr Gly Thr Thr Cys
1345                1350                1355                1360

Gly Ala Gly Gly Ala Ala Ala Ala Cys Cys Cys Thr Ala Thr Thr Ala
                1365                1370                1375

Ala Cys Gly Cys Cys Ala Gly Cys Gly Gly Gly Gly Thr Gly Gly Ala
            1380                1385                1390

Thr Gly Cys Gly Ala Ala Gly Gly Cys Cys Ala Thr Ala Cys Thr Thr
        1395                1400                1405

Ala Gly Cys Gly Cys Cys Ala Gly Gly Cys Thr Gly Ala Gly Cys Ala
    1410                1415                1420

Ala Ala Ala Gly Cys Ala Gly Gly Cys Gly Cys Thr Thr Gly Gly Ala
1425                1430                1435                1440

Gly Ala Ala Cys Cys Thr Gly Ala Thr Ala Gly Cys Cys Cys Ala Gly
                1445                1450                1455

Cys Thr Gly Cys Cys Cys Gly Gly Thr Gly Ala Ala Ala Ala Gly Ala
            1460                1465                1470

Ala Gly Ala Ala Cys Gly Gly Cys Cys Thr Cys Thr Thr Cys Gly Gly
        1475                1480                1485

Thr Ala Ala Thr Cys Thr Gly Ala Thr Thr Gly Cys Cys Cys Thr Gly
    1490                1495                1500

Ala Gly Cys Cys Thr Gly Gly Gly Cys Cys Thr Gly Ala Cys Cys Cys
1505                1510                1515                1520

Cys Cys Ala Ala Cys Thr Thr Cys Ala Ala Gly Ala Gly Cys Ala Ala
                1525                1530                1535

Cys Thr Thr Cys Gly Ala Cys Cys Thr Gly Gly Cys Ala Gly Ala Ala
            1540                1545                1550

Gly Ala Thr Gly Cys Cys Ala Ala Gly Cys Thr Gly Cys Ala Gly Thr
        1555                1560                1565
```

-continued

```
Thr Gly Ala Gly Thr Ala Ala Gly Gly Ala Cys Ala Cys Cys Thr Ala
    1570                1575                1580

Thr Gly Ala Cys Gly Ala Cys Gly Ala Cys Thr Thr Gly Gly Ala Cys
1585                1590                1595                1600

Ala Ala Thr Cys Thr Gly Cys Thr Cys Gly Cys Cys Cys Ala Ala Ala
                1605                1610                1615

Thr Cys Gly Gly Cys Gly Ala Cys Cys Ala Gly Thr Ala Cys Gly Cys
            1620                1625                1630

Thr Gly Ala Cys Cys Thr Gly Thr Thr Cys Cys Thr Cys Gly Cys Cys
        1635                1640                1645

Gly Cys Cys Ala Ala Gly Ala Ala Cys Cys Thr Thr Thr Cys Thr Gly
    1650                1655                1660

Ala Cys Gly Cys Ala Ala Thr Cys Cys Thr Gly Cys Thr Thr Ala Gly
1665                1670                1675                1680

Cys Gly Ala Thr Ala Thr Cys Cys Thr Thr Ala Gly Gly Gly Thr Gly
                1685                1690                1695

Ala Ala Cys Ala Cys Ala Gly Ala Gly Ala Thr Cys Ala Cys Cys Ala
            1700                1705                1710

Ala Gly Gly Cys Cys Cys Cys Cys Cys Thr Gly Ala Gly Cys Gly Cys
        1715                1720                1725

Cys Ala Gly Cys Ala Thr Gly Ala Thr Cys Ala Ala Gly Ala Gly Gly
    1730                1735                1740

Thr Ala Cys Gly Ala Cys Gly Ala Gly Cys Ala Cys Cys Ala Thr Cys
1745                1750                1755                1760

Ala Gly Gly Ala Cys Cys Thr Gly Ala Cys Cys Cys Thr Thr Cys Thr
                1765                1770                1775

Gly Ala Ala Gly Gly Cys Cys Cys Thr Gly Gly Thr Gly Ala Gly Gly
            1780                1785                1790

Cys Ala Gly Cys Ala Ala Cys Thr Gly Cys Cys Cys Gly Ala Gly Ala
        1795                1800                1805

Ala Gly Thr Ala Cys Ala Ala Gly Gly Ala Gly Ala Thr Cys Thr Thr
    1810                1815                1820

Thr Thr Thr Cys Gly Ala Cys Cys Ala Gly Ala Gly Cys Ala Ala Gly
1825                1830                1835                1840

Ala Ala Cys Gly Gly Cys Thr Ala Cys Gly Cys Cys Gly Gly Cys Thr
                1845                1850                1855

Ala Cys Ala Thr Cys Gly Ala Cys Gly Gly Cys Gly Gly Ala Gly Cys
            1860                1865                1870

Cys Ala Gly Cys Cys Ala Ala Gly Ala Gly Gly Ala Gly Thr Thr Cys
        1875                1880                1885

Thr Ala Cys Ala Ala Gly Thr Thr Cys Ala Thr Cys Ala Ala Gly Cys
    1890                1895                1900

Cys Cys Ala Thr Cys Cys Thr Gly Gly Ala Gly Ala Ala Gly Ala Thr
1905                1910                1915                1920

Gly Gly Ala Thr Gly Gly Cys Ala Cys Cys Gly Ala Gly Gly Ala Gly
                1925                1930                1935

Cys Thr Gly Cys Thr Gly Gly Thr Gly Ala Ala Gly Cys Thr Gly Ala
            1940                1945                1950

Ala Cys Ala Gly Gly Gly Ala Ala Gly Ala Thr Thr Thr Gly Cys Thr
        1955                1960                1965

Cys Cys Gly Gly Ala Ala Gly Cys Ala Gly Ala Gly Gly Ala Cys Cys
    1970                1975                1980

Thr Thr Thr Gly Ala Cys Ala Ala Cys Gly Gly Thr Ala Gly Cys Ala
```

-continued

```
1985                1990                1995                2000

Thr Cys Cys Cys Cys Cys Ala Cys Cys Ala Gly Ala Thr Cys Cys Ala
                2005                2010                2015

Cys Cys Thr Gly Gly Gly Cys Gly Ala Gly Cys Thr Gly Cys Ala Cys
            2020                2025                2030
Gly Cys Ala Ala Thr Ala Cys Thr Gly Ala Gly Gly Cys Gly Ala Cys
        2035                2040                2045

Ala Gly Gly Ala Gly Gly Ala Thr Thr Thr Cys Thr Ala Cys Cys Cys
    2050                2055                2060

Cys Thr Thr Cys Cys Thr Cys Ala Ala Gly Gly Ala Cys Ala Ala Thr
2065                2070                2075                2080

Ala Gly Gly Gly Ala Gly Ala Ala Ala Ala Thr Cys Gly Ala Ala Ala
                2085                2090                2095

Ala Gly Ala Thr Thr Cys Thr Gly Ala Cys Cys Thr Thr Cys Ala Gly
            2100                2105                2110

Gly Ala Thr Cys Cys Cys Cys Thr Ala Cys Thr Ala Cys Gly Thr Gly
        2115                2120                2125

Gly Gly Cys Cys Cys Thr Cys Thr Thr Gly Cys Cys Ala Gly Gly Gly
    2130                2135                2140

Gly Cys Ala Ala Cys Ala Gly Cys Cys Gly Ala Thr Thr Cys Gly Cys
2145                2150                2155                2160

Thr Thr Gly Gly Ala Thr Gly Ala Cys Ala Ala Gly Ala Ala Ala Gly
                2165                2170                2175

Ala Gly Cys Gly Ala Gly Gly Ala Gly Ala Cys Cys Ala Thr Cys Ala
            2180                2185                2190

Cys Cys Cys Cys Cys Thr Gly Gly Ala Ala Cys Thr Thr Cys Gly Ala
        2195                2200                2205

Gly Gly Ala Ala Gly Thr Gly Gly Thr Gly Gly Ala Cys Ala Ala Ala
    2210                2215                2220

Gly Gly Ala Gly Cys Ala Ala Gly Cys Gly Cys Gly Cys Ala Gly Thr
2225                2230                2235                2240

Cys Thr Thr Thr Cys Ala Thr Cys Gly Ala Ala Cys Gly Gly Ala Thr
                2245                2250                2255

Gly Ala Cys Cys Ala Ala Thr Thr Thr Cys Gly Ala Cys Ala Ala Ala
            2260                2265                2270

Ala Ala Cys Cys Thr Gly Cys Cys Thr Ala Ala Cys Gly Ala Gly Ala
        2275                2280                2285

Ala Gly Gly Thr Gly Cys Thr Gly Cys Cys Cys Ala Ala Gly Cys Ala
    2290                2295                2300

Cys Ala Gly Cys Cys Thr Gly Cys Thr Thr Thr Ala Cys Gly Ala Gly
2305                2310                2315                2320

Thr Ala Cys Thr Thr Cys Ala Cys Cys Gly Thr Gly Thr Ala Cys Ala
                2325                2330                2335

Ala Cys Gly Ala Gly Cys Thr Cys Ala Cys Cys Ala Ala Gly Gly Thr
            2340                2345                2350

Gly Ala Ala Ala Thr Ala Thr Gly Thr Gly Ala Cys Cys Gly Ala Gly
        2355                2360                2365

Gly Gly Cys Ala Thr Gly Cys Gly Ala Ala Ala Ala Cys Cys Cys Gly
    2370                2375                2380

Cys Thr Thr Thr Cys Cys Thr Gly Ala Gly Cys Gly Gly Cys Gly Ala
2385                2390                2395                2400

Gly Cys Ala Gly Ala Ala Gly Ala Ala Gly Gly Cys Cys Ala Thr Cys
                2405                2410                2415
```

```
Gly Thr Gly Gly Ala Cys Cys Thr Gly Cys Thr Gly Thr Cys Ala
            2420                2425                2430
Ala Gly Ala Cys Cys Ala Ala Cys Ala Gly Gly Ala Ala Gly Thr
            2435                2440                2445
Gly Ala Cys Cys Gly Thr Gly Ala Ala Gly Cys Ala Gly Cys Thr Gly
            2450                2455                2460
Ala Ala Gly Gly Ala Gly Gly Ala Cys Thr Ala Cys Thr Cys Ala
2465                2470                2475                2480
Ala Gly Ala Ala Gly Ala Thr Cys Gly Ala Gly Thr Gly Cys Thr Thr
            2485                2490                2495
Thr Gly Ala Thr Ala Gly Cys Gly Thr Gly Gly Ala Ala Ala Thr Ala
            2500                2505                2510
Ala Gly Cys Gly Gly Cys Gly Thr Gly Gly Ala Gly Gly Ala Cys Ala
            2515                2520                2525
Gly Gly Thr Thr Cys Ala Ala Cys Gly Cys Cys Ala Gly Cys Cys Thr
            2530                2535                2540
Gly Gly Gly Cys Ala Cys Cys Thr Ala Cys Ala Cys Gly Ala Cys
2545                2550                2555                2560
Thr Thr Gly Thr Thr Gly Ala Ala Gly Ala Thr Ala Ala Thr Cys Ala
            2565                2570                2575
Ala Ala Gly Ala Cys Ala Gly Gly Ala Thr Thr Thr Cys Cys Thr
            2580                2585                2590
Gly Gly Ala Thr Ala Ala Thr Gly Ala Gly Gly Ala Gly Ala Ala Cys
            2595                2600                2605
Gly Ala Gly Gly Ala Thr Ala Thr Ala Cys Thr Cys Gly Ala Gly Gly
            2610                2615                2620
Ala Cys Ala Thr Cys Gly Thr Gly Cys Thr Gly Ala Cys Thr Thr
2625                2630                2635                2640
Gly Ala Cys Cys Cys Thr Gly Thr Thr Thr Gly Ala Gly Gly Ala Cys
            2645                2650                2655
Cys Gly Ala Gly Ala Gly Ala Thr Gly Ala Thr Thr Gly Ala Ala Gly
            2660                2665                2670
Ala Ala Ala Gly Gly Cys Thr Cys Ala Ala Ala Cys Cys Thr Ala
            2675                2680                2685
Cys Gly Cys Cys Cys Ala Cys Cys Thr Gly Thr Thr Cys Gly Ala Cys
            2690                2695                2700
Gly Ala Cys Ala Ala Ala Gly Thr Gly Ala Thr Gly Ala Ala Ala Cys
2705                2710                2715                2720
Ala Ala Cys Thr Gly Ala Ala Gly Ala Gly Ala Cys Gly Ala Ala Gly
            2725                2730                2735
Ala Thr Ala Cys Ala Cys Cys Gly Gly Cys Thr Gly Gly Gly Gly Cys
            2740                2745                2750
Ala Gly Ala Cys Thr Gly Thr Cys Cys Ala Gly Gly Ala Ala Gly Cys
            2755                2760                2765
Thr Cys Ala Thr Cys Ala Ala Cys Gly Gly Cys Ala Thr Thr Ala Gly
            2770                2775                2780
Gly Gly Ala Cys Ala Ala Gly Cys Ala Gly Ala Gly Cys Gly Gly Cys
2785                2790                2795                2800
Ala Ala Gly Ala Cys Cys Ala Thr Cys Cys Thr Gly Gly Ala Thr Thr
            2805                2810                2815
Thr Cys Cys Thr Gly Ala Ala Gly Thr Cys Cys Gly Ala Cys Gly Gly
            2820                2825                2830
```

-continued

```
Cys Thr Thr Cys Gly Cys Cys Ala Ala Cys Cys Gly Ala Ala Ala Cys
        2835                2840                2845

Thr Thr Cys Ala Thr Gly Cys Ala Gly Cys Thr Gly Ala Thr Thr Cys
        2850                2855                2860

Ala Cys Gly Ala Thr Gly Ala Cys Ala Gly Cys Thr Thr Gly Ala Cys
2865                2870                2875                2880

Cys Thr Thr Cys Ala Ala Gly Gly Ala Gly Gly Ala Cys Ala Thr Cys
        2885                2890                2895

Cys Ala Gly Ala Ala Gly Gly Cys Cys Cys Ala Gly Gly Thr Thr Ala
        2900                2905                2910

Gly Cys Gly Gly Cys Cys Ala Gly Gly Gly Cys Gly Ala Cys Thr Cys
        2915                2920                2925

Cys Cys Thr Gly Cys Ala Cys Gly Ala Ala Cys Ala Thr Ala Thr Thr
        2930                2935                2940

Gly Cys Ala Ala Ala Cys Cys Thr Gly Gly Cys Ala Gly Gly Cys Thr
2945                2950                2955                2960

Cys Cys Cys Cys Thr Gly Cys Gly Ala Thr Cys Ala Ala Gly Ala Ala
        2965                2970                2975

Gly Gly Gly Cys Ala Thr Ala Cys Thr Gly Cys Ala Gly Ala Cys Cys
        2980                2985                2990

Gly Thr Thr Ala Ala Gly Gly Thr Thr Gly Thr Gly Ala Cys Gly Gly
        2995                3000                3005

Ala Ala Thr Thr Gly Gly Thr Cys Ala Ala Gly Gly Thr Cys Ala Thr
        3010                3015                3020

Gly Gly Gly Cys Ala Gly Gly Cys Ala Cys Ala Ala Gly Cys Cys Cys
3025                3030                3035                3040

Gly Ala Ala Ala Ala Cys Ala Thr Ala Gly Thr Thr Ala Thr Ala Gly
        3045                3050                3055

Ala Gly Ala Thr Gly Gly Cys Cys Ala Gly Ala Gly Ala Gly Ala Ala
        3060                3065                3070

Cys Cys Ala Gly Ala Cys Cys Ala Cys Cys Ala Ala Ala Ala Ala Gly
        3075                3080                3085

Gly Gly Cys Cys Ala Gly Ala Ala Gly Ala Ala Cys Ala Gly Cys Cys
        3090                3095                3100

Gly Gly Gly Ala Gly Cys Gly Cys Ala Thr Gly Ala Ala Ala Ala Gly
3105                3110                3115                3120

Gly Ala Thr Cys Gly Ala Gly Ala Gly Gly Gly Thr Ala Thr Cys
        3125                3130                3135

Ala Ala Gly Gly Ala Ala Cys Thr Cys Gly Gly Ala Ala Gly Cys Cys
        3140                3145                3150

Ala Gly Ala Thr Cys Cys Thr Cys Ala Ala Ala Gly Ala Gly Cys Ala
        3155                3160                3165

Cys Cys Cys Cys Gly Thr Gly Gly Ala Gly Ala Ala Thr Ala Cys Cys
        3170                3175                3180

Cys Ala Gly Cys Thr Cys Cys Ala Gly Ala Ala Cys Gly Ala Gly Ala
3185                3190                3195                3200

Ala Gly Cys Thr Gly Thr Ala Cys Cys Thr Gly Thr Ala Cys Thr Ala
        3205                3210                3215

Cys Cys Thr Gly Cys Ala Gly Ala Ala Cys Gly Gly Cys Ala Gly Gly
        3220                3225                3230

Gly Ala Cys Ala Thr Gly Thr Ala Cys Gly Thr Gly Ala Cys Cys
        3235                3240                3245

Ala Gly Gly Ala Gly Thr Thr Gly Gly Ala Cys Ala Thr Cys Ala Ala
```

-continued 3250 3255 3260

Cys Ala Gly Gly Cys Thr Thr Thr Cys Ala Gly Ala Cys Thr Ala Thr
3265 3270 3275 3280

Gly Ala Cys Gly Thr Gly Gly Ala Thr Gly Cys Cys Ala Thr Ala Gly
3285 3290 3295

Thr Gly Cys Cys Cys Cys Ala Gly Ala Gly Cys Thr Thr Thr Cys Thr
3300 3305 3310

Thr Ala Ala Ala Gly Ala Cys Gly Ala Thr Ala Gly Cys Ala Thr Cys
3315 3320 3325

Gly Ala Cys Ala Ala Cys Ala Ala Gly Gly Thr Cys Cys Thr Gly Ala
3330 3335 3340

Cys Cys Cys Gly Cys Thr Cys Cys Gly Ala Cys Ala Ala Ala Ala Ala
3345 3350 3355 3360

Cys Ala Gly Gly Gly Gly Cys Ala Ala Ala Ala Gly Cys Gly Ala Cys
3365 3370 3375

Ala Ala Cys Gly Thr Gly Cys Cys Ala Ala Gly Cys Gly Ala Ala Gly
3380 3385 3390

Ala Gly Gly Thr Gly Gly Thr Thr Ala Ala Ala Ala Ala Gly Ala Thr
3395 3400 3405

Gly Ala Ala Gly Ala Ala Cys Thr Ala Cys Thr Gly Gly Ala Gly Gly
3410 3415 3420

Cys Ala Ala Cys Thr Gly Cys Thr Cys Ala Ala Cys Gly Cys Gly Ala
3425 3430 3435 3440

Ala Ala Thr Thr Gly Ala Thr Cys Ala Cys Cys Cys Ala Gly Ala Gly
3445 3450 3455

Ala Ala Ala Gly Thr Thr Cys Gly Ala Thr Ala Ala Cys Cys Thr Gly
3460 3465 3470

Ala Cys Cys Ala Ala Gly Gly Cys Cys Gly Ala Gly Ala Gly Gly Gly
3475 3480 3485

Gly Cys Gly Gly Ala Cys Thr Cys Thr Cys Cys Gly Ala Ala Cys Thr
3490 3495 3500

Thr Gly Ala Cys Ala Ala Ala Gly Cys Gly Gly Gly Cys Thr Thr Cys
3505 3510 3515 3520

Ala Thr Ala Ala Ala Gly Ala Gly Gly Cys Ala Gly Cys Thr Gly Gly
3525 3530 3535

Thr Cys Gly Ala Gly Ala Cys Cys Cys Gly Ala Cys Ala Gly Ala Thr
3540 3545 3550

Cys Ala Cys Gly Ala Ala Gly Cys Ala Cys Gly Thr Gly Gly Cys Cys
3555 3560 3565

Cys Ala Ala Ala Thr Cys Cys Thr Cys Gly Ala Cys Ala Gly Cys Ala
3570 3575 3580

Gly Ala Ala Thr Gly Ala Ala Thr Ala Cys Cys Ala Ala Gly Thr Ala
3585 3590 3595 3600

Cys Gly Ala Thr Gly Ala Gly Ala Ala Thr Gly Ala Cys Ala Ala Ala
3605 3610 3615

Cys Thr Cys Ala Thr Cys Ala Gly Gly Gly Ala Ala Gly Thr Gly Ala
3620 3625 3630

Ala Ala Gly Thr Gly Ala Thr Thr Ala Cys Cys Cys Thr Gly Ala Ala
3635 3640 3645

Gly Ala Gly Cys Ala Ala Gly Thr Thr Gly Gly Thr Gly Thr Cys Cys
3650 3655 3660

Gly Ala Cys Thr Thr Thr Cys Gly Cys Ala Ala Ala Gly Ala Thr Thr
3665 3670 3675 3680

-continued

```
Thr Cys Cys Ala Gly Thr Thr Cys Thr Ala Cys Ala Ala Gly Gly Thr
                3685                3690                3695

Gly Ala Gly Gly Gly Ala Gly Ala Thr Cys Ala Ala Cys Ala Ala Cys
            3700                3705                3710

Thr Ala Cys Cys Ala Cys Cys Ala Thr Gly Cys Cys Cys Ala Cys Gly
        3715                3720                3725

Ala Cys Gly Cys Ala Thr Ala Cys Cys Thr Gly Ala Ala Cys Gly Cys
    3730                3735                3740

Cys Gly Thr Gly Gly Thr Cys Gly Gly Cys Ala Cys Cys Gly Cys Cys
3745                3750                3755                3760

Cys Thr Gly Ala Thr Thr Ala Ala Gly Ala Ala Gly Thr Ala Thr Cys
                3765                3770                3775

Cys Ala Ala Ala Gly Cys Thr Gly Gly Ala Gly Thr Cys Cys Gly Ala
            3780                3785                3790

Ala Thr Thr Thr Gly Thr Cys Thr Ala Cys Gly Gly Cys Gly Ala Cys
        3795                3800                3805

Thr Ala Cys Ala Ala Ala Gly Thr Thr Thr Ala Cys Gly Ala Thr Gly
    3810                3815                3820

Thr Gly Ala Gly Gly Ala Ala Gly Ala Thr Gly Ala Thr Cys Gly Cys
3825                3830                3835                3840

Thr Ala Ala Gly Ala Gly Cys Gly Ala Ala Cys Ala Gly Gly Ala Gly
                3845                3850                3855

Ala Thr Cys Gly Gly Cys Ala Ala Gly Gly Cys Cys Ala Cys Cys Gly
            3860                3865                3870

Cys Thr Ala Ala Gly Thr Ala Thr Thr Thr Cys Thr Thr Cys Thr Ala
        3875                3880                3885

Cys Ala Gly Cys Ala Ala Cys Ala Thr Cys Ala Thr Gly Ala Ala Cys
    3890                3895                3900

Thr Thr Thr Thr Thr Cys Ala Ala Gly Ala Cys Cys Gly Ala Gly Ala
3905                3910                3915                3920

Thr Cys Ala Cys Ala Cys Thr Thr Gly Cys Cys Ala Ala Cys Gly Gly
                3925                3930                3935

Cys Gly Ala Ala Ala Thr Cys Ala Gly Gly Ala Ala Gly Ala Gly Gly
            3940                3945                3950

Cys Cys Gly Cys Thr Thr Ala Thr Cys Gly Ala Gly Ala Cys Cys Ala
        3955                3960                3965

Ala Cys Gly Gly Thr Gly Ala Gly Ala Cys Cys Gly Gly Cys Gly Ala
    3970                3975                3980

Gly Ala Thr Cys Gly Thr Gly Thr Gly Gly Gly Ala Cys Ala Ala Gly
3985                3990                3995                4000

Gly Gly Cys Ala Gly Gly Gly Ala Cys Thr Thr Cys Gly Cys Cys Ala
                4005                4010                4015

Cys Cys Gly Thr Gly Ala Gly Gly Ala Ala Ala Gly Thr Cys Cys Thr
            4020                4025                4030

Gly Ala Gly Cys Ala Thr Gly Cys Cys Cys Cys Ala Gly Gly Thr Gly
        4035                4040                4045

Ala Ala Thr Ala Thr Thr Gly Thr Gly Ala Ala Ala Ala Ala Ala Ala
    4050                4055                4060

Cys Thr Gly Ala Gly Gly Thr Gly Cys Ala Gly Ala Cys Ala Gly Gly
4065                4070                4075                4080

Cys Gly Gly Cys Thr Thr Thr Ala Gly Cys Ala Ala Gly Gly Ala Ala
                4085                4090                4095
```

-continued

```
Thr Cys Cys Ala Thr Cys Cys Thr Gly Cys Cys Ala Ala Gly Ala
            4100                4105                4110

Gly Gly Ala Ala Cys Ala Gly Cys Gly Ala Cys Ala Ala Gly Cys Thr
        4115                4120                4125

Gly Ala Thr Cys Gly Cys Cys Gly Gly Ala Ala Gly Ala Ala Gly
    4130                4135                4140

Gly Ala Cys Thr Gly Gly Ala Cys Cys Thr Ala Ala Gly Ala
4145                4150                4155                4160

Ala Gly Thr Ala Thr Gly Gly Ala Gly Gly Cys Thr Thr Cys Gly Ala
                4165                4170                4175

Cys Ala Gly Cys Cys Cys Ala Cys Cys Gly Thr Ala Gly Cys Cys
            4180                4185                4190

Thr Ala Cys Ala Gly Cys Gly Thr Gly Cys Thr Gly Gly Thr Gly Gly
        4195                4200                4205

Thr Cys Gly Cys Gly Ala Ala Gly Gly Thr Ala Gly Ala Gly Ala Ala
    4210                4215                4220

Gly Gly Gly Gly Ala Ala Gly Ala Gly Cys Ala Ala Gly Ala Ala Ala
4225                4230                4235                4240

Cys Thr Gly Ala Ala Gly Ala Gly Cys Gly Thr Gly Ala Ala Gly Gly
                4245                4250                4255

Ala Gly Cys Thr Gly Cys Thr Cys Gly Gly Cys Ala Thr Ala Ala Cys
            4260                4265                4270

Cys Ala Thr Cys Ala Thr Gly Gly Ala Gly Ala Gly Gly Thr Cys Cys
        4275                4280                4285

Ala Gly Cys Thr Thr Thr Gly Ala Gly Ala Ala Gly Ala Ala Cys Cys
    4290                4295                4300

Cys Cys Ala Thr Thr Gly Ala Cys Thr Thr Thr Thr Gly Gly Ala
4305                4310                4315                4320

Ala Gly Cys Cys Ala Ala Gly Gly Cys Thr Ala Cys Ala Ala Ala
        4325                4330                4335

Gly Ala Gly Gly Thr Cys Ala Ala Ala Ala Gly Gly Ala Cys Cys
            4340                4345                4350

Thr Gly Ala Thr Cys Ala Thr Cys Ala Ala Cys Thr Cys Cys Cys
        4355                4360                4365

Cys Ala Ala Gly Thr Ala Cys Thr Cys Cys Thr Gly Thr Thr Thr
    4370                4375                4380

Gly Ala Ala Thr Thr Gly Gly Ala Gly Ala Ala Cys Gly Gly Cys Ala
4385                4390                4395                4400

Gly Ala Ala Ala Gly Ala Gly Gly Ala Thr Gly Cys Thr Gly Gly Cys
        4405                4410                4415

Gly Ala Gly Cys Gly Cys Thr Gly Gly Gly Ala Ala Cys Thr Gly
            4420                4425                4430

Cys Ala Ala Ala Ala Gly Gly Gly Cys Ala Ala Cys Gly Ala Ala Cys
        4435                4440                4445

Thr Gly Gly Cys Gly Cys Thr Gly Cys Cys Ala Gly Cys Ala Ala
    4450                4455                4460

Gly Thr Ala Cys Gly Thr Gly Ala Ala Thr Thr Thr Thr Cys Thr Gly
4465                4470                4475                4480

Thr Ala Cys Cys Thr Gly Gly Cys Gly Thr Cys Cys Ala Cys Thr
        4485                4490                4495

Ala Cys Gly Ala Ala Ala Ala Gly Cys Thr Gly Ala Ala Ala Gly Gly
            4500                4505                4510

Cys Ala Gly Cys Cys Cys Cys Gly Ala Gly Gly Ala Cys Ala Ala Cys
```

-continued

```
        4515                4520                4525

Gly Ala Gly Cys Ala Gly Ala Ala Gly Cys Ala Gly Cys Thr Gly Thr
    4530                4535                4540

Thr Cys Gly Thr Gly Gly Ala Gly Cys Ala Gly Cys Ala Cys Ala Ala
4545                4550                4555                4560

Gly Cys Ala Thr Thr Ala Cys Cys Thr Gly Gly Ala Cys Gly Ala Gly
                4565                4570                4575

Ala Thr Ala Ala Thr Cys Gly Ala Gly Cys Ala Ala Ala Thr Cys Ala
            4580                4585                4590

Gly Cys Gly Ala Gly Thr Thr Cys Ala Gly Cys Ala Ala Gly Ala Gly
        4595                4600                4605

Gly Gly Thr Gly Ala Thr Thr Cys Thr Gly Gly Cys Cys Gly Ala Cys
    4610                4615                4620

Gly Cys Gly Ala Ala Cys Cys Thr Gly Gly Ala Thr Ala Ala Gly Gly
4625                4630                4635                4640

Thr Cys Cys Thr Cys Ala Gly Cys Gly Cys Cys Thr Ala Cys Ala Ala
                4645                4650                4655

Cys Ala Ala Gly Cys Ala Cys Cys Gly Ala Gly Ala Cys Ala Ala Ala
            4660                4665                4670

Cys Cys Cys Ala Thr Cys Ala Gly Gly Gly Ala Gly Cys Ala Gly Gly
        4675                4680                4685

Cys Cys Gly Ala Gly Ala Ala Thr Ala Thr Cys Ala Thr Ala Cys Ala
    4690                4695                4700

Cys Cys Thr Gly Thr Thr Cys Ala Cys Cys Cys Thr Gly Ala Cys Ala
4705                4710                4715                4720

Ala Ala Thr Cys Thr Gly Gly Gly Cys Gly Cys Ala Cys Cys Thr Gly
                4725                4730                4735

Cys Gly Gly Cys Ala Thr Thr Cys Ala Ala Ala Thr Ala Cys Thr Thr
            4740                4745                4750

Cys Gly Ala Thr Ala Cys Cys Ala Cys Cys Ala Thr Cys Gly Ala Cys
        4755                4760                4765

Ala Gly Gly Ala Ala Ala Ala Gly Gly Thr Ala Cys Ala Cys Thr Ala
    4770                4775                4780

Gly Cys Ala Cys Thr Ala Ala Gly Gly Ala Gly Gly Thr Gly Cys Thr
4785                4790                4795                4800

Gly Gly Ala Thr Gly Cys Cys Ala Cys Cys Thr Thr Gly Ala Thr Cys
                4805                4810                4815

Cys Ala Cys Cys Ala Gly Thr Cys Cys Ala Thr Thr Ala Cys Cys Gly
            4820                4825                4830

Gly Cys Cys Thr Gly Thr Ala Thr Gly Ala Gly Ala Cys Cys Ala Gly
        4835                4840                4845

Gly Ala Thr Cys Gly Ala Cys Cys Thr Gly Ala Gly Cys Cys Ala Gly
    4850                4855                4860

Cys Thr Thr Gly Gly Ala Gly Gly Cys Gly Ala Cys Thr Cys Thr Ala
4865                4870                4875                4880

Gly Gly Gly Cys Gly Gly Ala Cys Cys Cys Ala Ala Ala Ala Ala Ala
                4885                4890                4895

Gly Ala Ala Ala Ala Gly Gly Ala Ala Gly Gly Thr Gly Gly Ala Ala
            4900                4905                4910

Thr Thr Cys Gly Ala Gly Gly Cys Cys Ala Gly Cys Gly Gly Thr Thr
        4915                4920                4925

Cys Cys Gly Gly Ala Cys Gly Gly Gly Cys Thr Gly Ala Cys Gly Cys
    4930                4935                4940
```

-continued

```
Ala Thr Thr Gly Gly Ala Cys Gly Ala Thr Thr Thr Thr Gly Ala Thr
4945                4950                4955                4960

Cys Thr Gly Gly Ala Thr Ala Thr Gly Cys Thr Gly Gly Gly Ala Ala
                4965                4970                4975

Gly Thr Gly Ala Cys Gly Cys Cys Cys Thr Cys Gly Ala Thr Gly Ala
            4980                4985                4990

Thr Thr Thr Thr Gly Ala Cys Cys Thr Thr Gly Ala Cys Ala Thr Gly
        4995                5000                5005

Cys Thr Thr Gly Gly Thr Thr Cys Gly Gly Ala Thr Gly Cys Cys Cys
    5010                5015                5020

Thr Thr Gly Ala Thr Gly Ala Cys Thr Thr Thr Gly Ala Cys Cys Thr
5025                5030                5035                5040

Cys Gly Ala Cys Ala Thr Gly Cys Thr Cys Gly Gly Cys Ala Gly Thr
                5045                5050                5055

Gly Ala Cys Gly Cys Cys Cys Thr Thr Gly Ala Thr Gly Ala Thr Thr
            5060                5065                5070

Thr Cys Gly Ala Cys Cys Thr Gly Gly Ala Cys Ala Thr Gly Cys Thr
        5075                5080                5085

Cys Gly Gly Cys Ala Gly Cys Gly Ala Gly Thr Thr Cys Thr Cys Thr
    5090                5095                5100

Ala Gly Ala Gly Gly Cys Ala Gly Thr Gly Gly Ala Gly Ala Gly Gly
5105                5110                5115                5120

Gly Cys Ala Gly Ala Gly Gly Ala Ala Gly Thr Cys Thr Gly Cys Thr
                5125                5130                5135

Ala Ala Cys Ala Thr Gly Cys Gly Gly Thr Gly Ala Cys Gly Thr Cys
            5140                5145                5150

Gly Ala Gly Gly Ala Gly Ala Ala Thr Cys Cys Thr Gly Gly Cys Cys
        5155                5160                5165

Cys Ala Ala Thr Gly Gly Cys Thr Thr Cys Ala Ala Ala Cys Thr Thr
    5170                5175                5180

Thr Ala Cys Thr Cys Ala Gly Thr Thr Cys Gly Thr Gly Cys Thr Cys
5185                5190                5195                5200

Gly Thr Gly Gly Ala Cys Ala Ala Thr Gly Gly Thr Gly Gly Gly Ala
                5205                5210                5215

Cys Ala Gly Gly Gly Gly Ala Thr Gly Thr Gly Ala Cys Ala Gly Thr
            5220                5225                5230

Gly Gly Cys Thr Cys Cys Thr Thr Cys Thr Ala Ala Thr Thr Thr Cys
        5235                5240                5245

Gly Cys Thr Ala Ala Thr Gly Gly Gly Gly Thr Gly Gly Cys Ala Gly
    5250                5255                5260

Ala Gly Thr Gly Gly Ala Thr Cys Ala Gly Cys Thr Cys Cys Ala Ala
5265                5270                5275                5280

Cys Thr Cys Ala Cys Gly Gly Ala Gly Cys Cys Ala Gly Gly Cys Cys
                5285                5290                5295

Thr Ala Cys Ala Ala Gly Gly Thr Gly Ala Cys Ala Thr Gly Cys Ala
            5300                5305                5310

Gly Cys Gly Thr Cys Ala Gly Gly Cys Ala Gly Thr Cys Thr Ala Gly
        5315                5320                5325

Thr Gly Cys Cys Cys Ala Gly Ala Ala Gly Ala Gly Ala Ala Ala Gly
    5330                5335                5340

Thr Ala Thr Ala Cys Cys Ala Thr Cys Ala Ala Gly Gly Thr Gly Gly
5345                5350                5355                5360
```

-continued

Ala Gly Gly Thr Cys Cys Cys Ala Ala Ala Gly Thr Gly Gly Cys
            5365                5370            5375

Thr Ala Cys Cys Cys Ala Gly Ala Cys Ala Gly Thr Gly Gly Cys
        5380                5385            5390

Gly Gly Ala Gly Thr Cys Gly Ala Ala Cys Thr Gly Cys Cys Thr Gly
        5395                5400            5405

Thr Cys Gly Cys Cys Gly Cys Thr Gly Gly Ala Gly Gly Thr Cys
        5410                5415            5420

Cys Thr Ala Cys Cys Thr Gly Ala Ala Cys Ala Thr Gly Gly Ala Gly
5425            5430                5435                5440

Cys Thr Cys Ala Cys Thr Ala Thr Cys Cys Ala Ala Thr Thr Thr
            5445                5450                5455

Thr Cys Gly Cys Thr Ala Cys Cys Ala Ala Thr Thr Cys Thr Gly Ala
            5460                5465            5470

Cys Gly Thr Gly Ala Ala Cys Thr Cys Ala Thr Cys Gly Thr Gly
        5475                5480            5485

Ala Ala Gly Gly Cys Ala Ala Thr Gly Cys Ala Gly Gly Gly Gly Cys
        5490                5495            5500

Thr Cys Cys Thr Cys Ala Ala Ala Gly Ala Cys Gly Gly Thr Ala Ala
5505            5510                5515                5520

Thr Cys Cys Thr Ala Thr Cys Cys Cys Thr Thr Cys Gly Cys Cys
            5525                5530            5535

Ala Thr Cys Gly Cys Cys Gly Cys Thr Ala Ala Cys Thr Cys Ala Gly
        5540                5545            5550

Gly Thr Ala Thr Cys Thr Ala Cys Ala Gly Cys Gly Cys Thr Gly Gly
        5555                5560            5565

Ala Gly Gly Ala Gly Gly Thr Gly Gly Ala Ala Gly Cys Gly Gly Ala
        5570                5575            5580

Gly Gly Ala Gly Gly Ala Gly Gly Ala Ala Gly Cys Gly Gly Ala Gly
5585            5590                5595                5600

Gly Ala Gly Gly Ala Gly Gly Thr Ala Gly Cys Gly Gly Ala Cys Cys
        5605                5610            5615

Thr Ala Ala Gly Ala Ala Ala Ala Gly Ala Gly Gly Ala Ala Gly
        5620                5625            5630

Gly Thr Gly Gly Cys Gly Gly Cys Cys Gly Cys Thr Gly Gly Ala Thr
        5635                5640            5645

Cys Cys Cys Cys Thr Thr Cys Ala Gly Gly Cys Ala Gly Ala Thr
            5650                5655            5660

Cys Ala Gly Cys Ala Ala Cys Cys Ala Gly Gly Cys Cys Cys Thr Gly
5665            5670                5675                5680

Gly Cys Thr Cys Thr Gly Gly Cys Cys Cys Thr Ala Gly Cys Thr
            5685                5690            5695

Cys Cys Gly Cys Thr Cys Cys Ala Gly Thr Gly Cys Thr Gly Gly Cys
        5700                5705            5710

Cys Cys Ala Gly Ala Cys Thr Ala Thr Gly Gly Thr Gly Cys Cys Cys
            5715                5720            5725

Thr Cys Thr Ala Gly Thr Gly Cys Thr Ala Thr Gly Gly Thr Gly Cys
            5730                5735            5740

Cys Thr Cys Thr Gly Gly Cys Cys Ala Gly Cys Cys Ala Cys Cys
5745            5750                5755                5760

Thr Gly Cys Thr Cys Cys Ala Gly Cys Cys Cys Thr Gly Thr Gly
            5765                5770            5775

Cys Thr Gly Ala Cys Cys Cys Cys Ala Gly Gly Ala Cys Cys Ala Cys

-continued

```
           5780                5785                5790
Cys Cys Cys Ala Gly Thr Cys Ala Cys Thr Gly Ala Gly Cys Gly Cys
           5795                5800                5805
Thr Cys Cys Ala Gly Thr Gly Cys Cys Ala Ala Gly Thr Cys Thr
           5810                5815           5820
Ala Cys Ala Cys Ala Gly Gly Cys Cys Gly Cys Gly Ala Gly Gly
5825            5830                5835                5840
Gly Gly Ala Cys Thr Cys Thr Gly Ala Gly Thr Gly Ala Ala Gly Cys
           5845                5850                5855
Thr Cys Thr Gly Cys Thr Gly Cys Ala Cys Cys Thr Gly Cys Ala Gly
           5860                5865                5870
Thr Thr Cys Gly Ala Cys Gly Cys Thr Gly Ala Thr Gly Ala Gly Gly
           5875                5880                5885
Ala Cys Cys Thr Gly Gly Gly Ala Gly Cys Thr Cys Thr Gly Cys Thr
           5890                5895                5900
Gly Gly Gly Gly Ala Ala Cys Ala Gly Cys Ala Cys Gly Ala Thr
5905            5910                5915                5920
Cys Cys Cys Gly Gly Ala Gly Thr Gly Thr Cys Ala Cys Ala Gly
           5925                5930                5935
Ala Thr Cys Thr Gly Gly Cys Cys Thr Cys Cys Gly Thr Gly Gly Ala
           5940                5945                5950
Cys Ala Ala Cys Thr Cys Thr Gly Ala Gly Thr Thr Thr Cys Ala Gly
           5955                5960                5965
Cys Ala Gly Cys Thr Gly Cys Thr Gly Ala Ala Thr Cys Ala Gly Gly
           5970                5975                5980
Gly Cys Gly Thr Gly Thr Cys Cys Ala Thr Gly Thr Cys Thr Cys Ala
5985            5990                5995                6000
Thr Ala Gly Thr Ala Cys Ala Gly Cys Cys Gly Ala Ala Cys Cys Ala
           6005                6010                6015
Ala Thr Gly Cys Thr Gly Ala Thr Gly Gly Ala Gly Thr Ala Cys Cys
           6020                6025                6030
Cys Cys Gly Ala Ala Gly Cys Cys Ala Thr Thr Ala Cys Cys Cys Gly
           6035                6040                6045
Gly Cys Thr Gly Gly Thr Gly Ala Cys Cys Gly Gly Cys Ala Gly Cys
           6050                6055                6060
Cys Ala Gly Cys Gly Gly Cys Cys Cys Cys Cys Gly Ala Cys Cys
6065            6070                6075                6080
Cys Cys Gly Cys Thr Cys Cys Ala Ala Cys Thr Cys Cys Cys Thr
           6085                6090                6095
Gly Gly Gly Ala Ala Cys Cys Ala Gly Cys Gly Gly Cys Cys Thr Gly
           6100                6105                6110
Cys Cys Thr Ala Ala Thr Gly Gly Gly Cys Thr Gly Thr Cys Cys Gly
           6115                6120                6125
Gly Ala Gly Ala Thr Gly Ala Gly Gly Ala Cys Thr Thr Cys Thr Cys
           6130                6135                6140
Ala Ala Gly Cys Ala Thr Cys Gly Cys Thr Gly Ala Thr Ala Thr Gly
6145            6150                6155                6160
Gly Ala Cys Thr Thr Thr Ala Gly Thr Gly Cys Cys Cys Thr Gly Cys
           6165                6170                6175
Thr Gly Thr Cys Ala Cys Ala Gly Ala Thr Thr Thr Cys Cys Thr Cys
           6180                6185                6190
Thr Ala Gly Thr Gly Gly Gly Cys Ala Gly Gly Ala Gly Gly Ala
           6195                6200                6205
```

Gly Gly Thr Gly Gly Ala Ala Gly Cys Gly Gly Cys Thr Cys Ala
         6210                6215                6220

Gly Cys Gly Thr Gly Gly Ala Cys Ala Cys Ala Gly Thr Gly Cys
6225                6230                6235                6240

Cys Cys Thr Gly Cys Thr Gly Gly Ala Cys Cys Thr Gly Thr Cys
              6245                6250                6255

Ala Gly Cys Cys Cys Cys Thr Cys Gly Gly Thr Gly Ala Cys Cys Gly
         6260                6265                6270

Thr Gly Cys Cys Cys Gly Ala Cys Ala Thr Gly Ala Gly Cys Cys Thr
              6275                6280                6285

Gly Cys Cys Thr Gly Ala Cys Cys Thr Gly Ala Cys Ala Gly Cys
         6290                6295                6300

Ala Gly Cys Cys Thr Gly Gly Cys Cys Ala Gly Thr Ala Thr Cys Cys
6305 6310 6315 6320

Ala Ala Gly Ala Gly Cys Thr Cys Cys Thr Gly Thr Cys Thr Cys Cys
6325 6330 6335

Cys Cys Ala Gly Gly Ala Gly Cys Cys Cys Cys Cys Ala Gly Gly
6340 6345 6350

Cys Cys Thr Cys Cys Cys Gly Ala Gly Gly Cys Ala Gly Ala Gly Ala
6355 6360 6365

Ala Cys Ala Gly Cys Ala Gly Cys Cys Cys Gly Gly Ala Thr Thr Cys
6370 6375 6380

Ala Gly Gly Gly Ala Ala Gly Cys Ala Gly Cys Thr Gly Gly Thr Gly
6385 6390 6395 6400

Cys Ala Cys Thr Ala Cys Ala Cys Ala Gly Cys Gly Cys Ala Gly Cys
6405 6410 6415

Cys Gly Cys Thr Gly Thr Thr Cys Cys Thr Gly Cys Thr Gly Gly Ala
6420 6425 6430

Cys Cys Cys Cys Gly Gly Cys Thr Cys Cys Gly Thr Gly Gly Ala Cys
6435 6440 6445

Ala Cys Cys Gly Gly Gly Ala Gly Cys Ala Ala Cys Gly Ala Cys Cys
6450 6455 6460

Thr Gly Cys Cys Gly Gly Thr Gly Cys Thr Gly Thr Thr Thr Gly Ala
6465 6470 6475 6480

Gly Cys Thr Gly Gly Gly Ala Gly Ala Gly Gly Gly Cys Thr Cys Cys
6485 6490 6495

Thr Ala Cys Thr Thr Cys Thr Cys Cys Gly Ala Ala Gly Gly Gly Gly
6500 6505 6510

Ala Cys Gly Gly Cys Thr Thr Cys Gly Cys Cys Gly Ala Gly Gly Ala
6515 6520 6525

Cys Cys Cys Cys Ala Cys Cys Ala Thr Cys Thr Cys Cys Cys Thr Gly
6530 6535 6540

Cys Thr Gly Ala Cys Ala Gly Gly Cys Thr Cys Gly Gly Ala Gly Cys
6545 6550 6555 6560

Cys Thr Cys Cys Cys Ala Ala Ala Gly Cys Cys Ala Ala Gly Gly Ala
6565 6570 6575

Cys Cys Cys Cys Ala Cys Thr Gly Thr Cys Thr Cys Cys Gly Ala Ala
6580 6585 6590

Gly Cys Thr Thr Gly Ala
6595

<210> SEQ ID NO 2
<211> LENGTH: 264

<212> TYPE: RNA
<213> ORGANISM: streptococcus pyogenes

<400> SEQUENCE: 2

```
aaggtcgggc aggaagaggg cctatttccc atgattcctt catatttgca tatacgatac    60
aaggctgtta gagagataat tagaattaat ttgactgtaa acacaaagat attagtacaa   120
aatacgtgac gtagaaagta ataatttctt gggtagtttg cagttttaaa attatgtttt   180
aaaatggact atcatatgct taccgtaact tgaaagtatt tcgatttctt ggctttatat   240
atcttgtgga aggacgaaa cacc                                           264
```

<210> SEQ ID NO 3
<211> LENGTH: 161
<212> TYPE: RNA
<213> ORGANISM: streptococcus pyogenes

<400> SEQUENCE: 3

```
ggggtgggac tggagcccag gttttagagc taggccaaca tgaggatcac ccatgtctgc    60
agggcctagc aagttaaaat aaggctagtc cgttatcaac ttggccaaca tgaggatcac   120
ccatgtctgc agggccaagt ggcaccgagt cggtgctttt t                       161
```

<210> SEQ ID NO 4
<211> LENGTH: 162
<212> TYPE: RNA
<213> ORGANISM: streptococcus pyogenes

<400> SEQUENCE: 4

```
gcgtcctgcc cagttcctga ggttttagag ctaggccaac atgaggatca cccatgtctg    60
cagggcctag caagttaaaa taaggctagt ccgttatcaa cttggccaac atgaggatca   120
cccatgtctg cagggccaag tggcaccgag tcggtgcttt tt                      162
```

<210> SEQ ID NO 5
<211> LENGTH: 162
<212> TYPE: RNA
<213> ORGANISM: streptococcus pyogenes

<400> SEQUENCE: 5

```
gaagggtcac tgggtgccac cgttttagag ctaggccaac atgaggatca cccatgtctg    60
cagggcctag caagttaaaa taaggctagt ccgttatcaa cttggccaac atgaggatca   120
cccatgtctg cagggccaag tggcaccgag tcggtgcttt tt                      162
```

<210> SEQ ID NO 6
<211> LENGTH: 162
<212> TYPE: RNA
<213> ORGANISM: streptococcus pyogenes

<400> SEQUENCE: 6

```
gccacgctct gtgacttcac cgttttagag ctaggccaac atgaggatca cccatgtctg    60
cagggcctag caagttaaaa taaggctagt ccgttatcaa cttggccaac atgaggatca   120
cccatgtctg cagggccaag tggcaccgag tcggtgcttt tt                      162
```

<210> SEQ ID NO 7
<211> LENGTH: 161
<212> TYPE: RNA
<213> ORGANISM: streptococcus pyogenes

<400> SEQUENCE: 7

```
ggtttcagaa cttttacct gttttagagc taggccaaca tgaggatcac ccatgtctgc      60
agggcctagc aagttaaaat aaggctagtc cgttatcaac ttggccaaca tgaggatcac    120
ccatgtctgc agggccaagt ggcaccgagt cggtgctttt t                        161

<210> SEQ ID NO 8
<211> LENGTH: 162
<212> TYPE: RNA
<213> ORGANISM: streptococcus pyogenes

<400> SEQUENCE: 8
gagaaacctc gcgaccagcc agttttagag ctaggccaac atgaggatca cccatgtctg     60
cagggcctag caagttaaaa taaggctagt ccgttatcaa cttggccaac atgaggatca    120
cccatgtctg cagggccaag tggcaccgag tcggtgcttt tt                       162

<210> SEQ ID NO 9
<211> LENGTH: 161
<212> TYPE: RNA
<213> ORGANISM: streptococcus pyogenes

<400> SEQUENCE: 9
ggttccagcc gatctggtcg gttttagagc taggccaaca tgaggatcac ccatgtctgc     60
agggcctagc aagttaaaat aaggctagtc cgttatcaac ttggccaaca tgaggatcac   120
ccatgtctgc agggccaagt ggcaccgagt cggtgctttt t                        161

<210> SEQ ID NO 10
<211> LENGTH: 161
<212> TYPE: RNA
<213> ORGANISM: streptococcus pyogenes

<400> SEQUENCE: 10
ggcgtccggc gtggactgga gttttagagc taggccaaca tgaggatcac ccatgtctgc     60
agggcctagc aagttaaaat aaggctagtc cgttatcaac ttggccaaca tgaggatcac   120
ccatgtctgc agggccaagt ggcaccgagt cggtgctttt t                        161

<210> SEQ ID NO 11
<211> LENGTH: 161
<212> TYPE: RNA
<213> ORGANISM: streptococcus pyogenes

<400> SEQUENCE: 11
ggtcgcggtg ttgggtctcc gttttagagc taggccaaca tgaggatcac ccatgtctgc     60
agggcctagc aagttaaaat aaggctagtc cgttatcaac ttggccaaca tgaggatcac   120
ccatgtctgc agggccaagt ggcaccgagt cggtgctttt t                        161

<210> SEQ ID NO 12
<211> LENGTH: 161
<212> TYPE: RNA
<213> ORGANISM: streptococcus pyogenes

<400> SEQUENCE: 12
ggtcgggcta gggatcgggc gttttagagc taggccaaca tgaggatcac ccatgtctgc     60
agggcctagc aagttaaaat aaggctagtc cgttatcaac ttggccaaca tgaggatcac   120
ccatgtctgc agggccaagt ggcaccgagt cggtgctttt t                        161

<210> SEQ ID NO 13
<211> LENGTH: 161
```

<212> TYPE: RNA
<213> ORGANISM: streptococcus pyogenes

<400> SEQUENCE: 13
ggtagtagtc cccgagggca gttttagagc taggccaaca tgaggatcac ccatgtctgc    60
agggcctagc aagttaaaat aaggctagtc cgttatcaac ttggccaaca tgaggatcac   120
ccatgtctgc agggccaagt ggcaccgagt cggtgctttt t                       161

<210> SEQ ID NO 14
<211> LENGTH: 161
<212> TYPE: RNA
<213> ORGANISM: streptococcus pyogenes

<400> SEQUENCE: 14
gtcctgcctc actggagaat gttttagagc taggccaaca tgaggatcac ccatgtctgc    60
agggcctagc aagttaaaat aaggctagtc cgttatcaac ttggccaaca tgaggatcac   120
ccatgtctgc agggccaagt ggcaccgagt cggtgctttt t                       161

<210> SEQ ID NO 15
<211> LENGTH: 161
<212> TYPE: RNA
<213> ORGANISM: streptococcus pyogenes

<400> SEQUENCE: 15
gatggtcctg ccaccgactg gttttagagc taggccaaca tgaggatcac ccatgtctgc    60
agggcctagc aagttaaaat aaggctagtc cgttatcaac ttggccaaca tgaggatcac   120
ccatgtctgc agggccaagt ggcaccgagt cggtgctttt t                       161

<210> SEQ ID NO 16
<211> LENGTH: 162
<212> TYPE: RNA
<213> ORGANISM: streptococcus pyogenes

<400> SEQUENCE: 16
gcaaacctct ccacctgctc cgttttagag ctaggccaac atgaggatca cccatgtctg    60
cagggcctag caagttaaaa taaggctagt ccgttatcaa cttggccaac atgaggatca   120
cccatgtctg cagggccaag tggcaccgag tcggtgcttt tt                      162

<210> SEQ ID NO 17
<211> LENGTH: 162
<212> TYPE: RNA
<213> ORGANISM: streptococcus pyogenes

<400> SEQUENCE: 17
gtgggggccc agagggagga agtttagag ctaggccaac atgaggatca cccatgtctg     60
cagggcctag caagttaaaa taaggctagt ccgttatcaa cttggccaac atgaggatca   120
cccatgtctg cagggccaag tggcaccgag tcggtgcttt tt                      162

<210> SEQ ID NO 18
<211> LENGTH: 162
<212> TYPE: RNA
<213> ORGANISM: streptococcus pyogenes

<400> SEQUENCE: 18
gatgctctct ctttccaaat agttttagag ctaggccaac atgaggatca cccatgtctg    60
cagggcctag caagttaaaa taaggctagt ccgttatcaa cttggccaac atgaggatca   120

```
cccatgtctg cagggccaag tggcaccgag tcggtgcttt tt                          162

<210> SEQ ID NO 19
<211> LENGTH: 162
<212> TYPE: RNA
<213> ORGANISM: streptococcus pyogenes

<400> SEQUENCE: 19
gcctgaaata tttgaaatgt cgttttagag ctaggccaac atgaggatca cccatgtctg       60
cagggcctag caagttaaaa taaggctagt ccgttatcaa cttggccaac atgaggatca      120
cccatgtctg cagggccaag tggcaccgag tcggtgcttt tt                          162

<210> SEQ ID NO 20
<211> LENGTH: 161
<212> TYPE: RNA
<213> ORGANISM: streptococcus pyogenes

<400> SEQUENCE: 20
gccccagggt gtggcaagtg gttttagagc taggccaaca tgaggatcac ccatgtctgc       60
agggcctagc aagttaaaat aaggctagtc cgttatcaac ttggccaaca tgaggatcac      120
ccatgtctgc agggccaagt ggcaccgagt cggtgctttt t                           161

<210> SEQ ID NO 21
<211> LENGTH: 162
<212> TYPE: RNA
<213> ORGANISM: streptococcus pyogenes

<400> SEQUENCE: 21
gccaggaagc gaggacacca cgttttagag ctaggccaac atgaggatca cccatgtctg       60
cagggcctag caagttaaaa taaggctagt ccgttatcaa cttggccaac atgaggatca      120
cccatgtctg cagggccaag tggcaccgag tcggtgcttt tt                          162

<210> SEQ ID NO 22
<211> LENGTH: 162
<212> TYPE: RNA
<213> ORGANISM: streptococcus pyogenes

<400> SEQUENCE: 22
gtctgacgcg cacaaacttt cgttttagag ctaggccaac atgaggatca cccatgtctg       60
cagggcctag caagttaaaa taaggctagt ccgttatcaa cttggccaac atgaggatca      120
cccatgtctg cagggccaag tggcaccgag tcggtgcttt tt                          162

<210> SEQ ID NO 23
<211> LENGTH: 162
<212> TYPE: RNA
<213> ORGANISM: streptococcus pyogenes

<400> SEQUENCE: 23
gacaggcagg gaacaaggcc agttttagag ctaggccaac atgaggatca cccatgtctg       60
cagggcctag caagttaaaa taaggctagt ccgttatcaa cttggccaac atgaggatca      120
cccatgtctg cagggccaag tggcaccgag tcggtgcttt tt                          162

<210> SEQ ID NO 24
<211> LENGTH: 162
<212> TYPE: RNA
<213> ORGANISM: streptococcus pyogenes

<400> SEQUENCE: 24
```

```
gctctcctct ccacagcctg cgttttagag ctaggccaac atgaggatca cccatgtctg    60
cagggcctag caagttaaaa taaggctagt ccgttatcaa cttggccaac atgaggatca   120
cccatgtctg cagggccaag tggcaccgag tcggtgcttt tt                      162

<210> SEQ ID NO 25
<211> LENGTH: 162
<212> TYPE: RNA
<213> ORGANISM: streptococcus pyogenes

<400> SEQUENCE: 25
gcttatgaaa agccccaggg cgttttagag ctaggccaac atgaggatca cccatgtctg    60
cagggcctag caagttaaaa taaggctagt ccgttatcaa cttggccaac atgaggatca   120
cccatgtctg cagggccaag tggcaccgag tcggtgcttt tt                      162

<210> SEQ ID NO 26
<211> LENGTH: 162
<212> TYPE: RNA
<213> ORGANISM: streptococcus pyogenes

<400> SEQUENCE: 26
gatccctgct gccccggct cgttttagag ctaggccaac atgaggatca cccatgtctg     60
cagggcctag caagttaaaa taaggctagt ccgttatcaa cttggccaac atgaggatca   120
cccatgtctg cagggccaag tggcaccgag tcggtgcttt tt                      162

<210> SEQ ID NO 27
<211> LENGTH: 161
<212> TYPE: RNA
<213> ORGANISM: streptococcus pyogenes

<400> SEQUENCE: 27
gcatgtgcca tatgcatgtg gttttagagc taggccaaca tgaggatcac ccatgtctgc    60
agggcctagc aagttaaaat aaggctagtc cgttatcaac ttggccaaca tgaggatcac   120
ccatgtctgc agggccaagt ggcaccgagt cggtgctttt t                       161

<210> SEQ ID NO 28
<211> LENGTH: 162
<212> TYPE: RNA
<213> ORGANISM: streptococcus pyogenes

<400> SEQUENCE: 28
gacacgcgaa tggcacatgc agttttagag ctaggccaac atgaggatca cccatgtctg    60
cagggcctag caagttaaaa taaggctagt ccgttatcaa cttggccaac atgaggatca   120
cccatgtctg cagggccaag tggcaccgag tcggtgcttt tt                      162

<210> SEQ ID NO 29
<211> LENGTH: 161
<212> TYPE: RNA
<213> ORGANISM: streptococcus pyogenes

<400> SEQUENCE: 29
gcatgtatgc tgtgcacgtg gttttagagc taggccaaca tgaggatcac ccatgtctgc    60
agggcctagc aagttaaaat aaggctagtc cgttatcaac ttggccaaca tgaggatcac   120
ccatgtctgc agggccaagt ggcaccgagt cggtgctttt t                       161

<210> SEQ ID NO 30
```

```
<211> LENGTH: 161
<212> TYPE: RNA
<213> ORGANISM: streptococcus pyogenes

<400> SEQUENCE: 30
gcttgcgtgc catgcatgtg gttttagagc taggccaaca tgaggatcac ccatgtctgc      60
agggcctagc aagttaaaat aaggctagtc cgttatcaac ttggccaaca tgaggatcac     120
ccatgtctgc agggccaagt ggcaccgagt cggtgctttt t                         161

<210> SEQ ID NO 31
<211> LENGTH: 162
<212> TYPE: RNA
<213> ORGANISM: streptococcus pyogenes

<400> SEQUENCE: 31
gcatggtaca cgcaaagcac agttttagag ctaggccaac atgaggatca cccatgtctg      60
cagggcctag caagttaaaa taaggctagt ccgttatcaa cttggccaac atgaggatca     120
cccatgtctg cagggccaag tggcaccgag tcggtgcttt tt                        162

<210> SEQ ID NO 32
<211> LENGTH: 161
<212> TYPE: RNA
<213> ORGANISM: streptococcus pyogenes

<400> SEQUENCE: 32
gcattaggga atggactgct gttttagagc taggccaaca tgaggatcac ccatgtctgc      60
agggcctagc aagttaaaat aaggctagtc cgttatcaac ttggccaaca tgaggatcac     120
ccatgtctgc agggccaagt ggcaccgagt cggtgctttt t                         161

<210> SEQ ID NO 33
<211> LENGTH: 162
<212> TYPE: RNA
<213> ORGANISM: streptococcus pyogenes

<400> SEQUENCE: 33
gctaagattc tgctttgact agttttagag ctaggccaac atgaggatca cccatgtctg      60
cagggcctag caagttaaaa taaggctagt ccgttatcaa cttggccaac atgaggatca     120
cccatgtctg cagggccaag tggcaccgag tcggtgcttt tt                        162

<210> SEQ ID NO 34
<211> LENGTH: 162
<212> TYPE: RNA
<213> ORGANISM: streptococcus pyogenes

<400> SEQUENCE: 34
gttctcatct gtcacctgat cgttttagag ctaggccaac atgaggatca cccatgtctg      60
cagggcctag caagttaaaa taaggctagt ccgttatcaa cttggccaac atgaggatca     120
cccatgtctg cagggccaag tggcaccgag tcggtgcttt tt                        162

<210> SEQ ID NO 35
<211> LENGTH: 162
<212> TYPE: RNA
<213> ORGANISM: streptococcus pyogenes

<400> SEQUENCE: 35
gcctctctag cctccatcag ggttttagag ctaggccaac atgaggatca cccatgtctg      60
cagggcctag caagttaaaa taaggctagt ccgttatcaa cttggccaac atgaggatca     120
```

```
cccatgtctg cagggccaag tggcaccgag tcggtgcttt tt              162
```

<210> SEQ ID NO 36
<211> LENGTH: 162
<212> TYPE: RNA
<213> ORGANISM: streptococcus pyogenes

<400> SEQUENCE: 36

```
gtcgggcaca tcttcgaaaa cgttttagag ctaggccaac atgaggatca cccatgtctg   60
cagggcctag caagttaaaa taaggctagt ccgttatcaa cttggccaac atgaggatca  120
cccatgtctg cagggccaag tggcaccgag tcggtgcttt tt                     162
```

<210> SEQ ID NO 37
<211> LENGTH: 162
<212> TYPE: RNA
<213> ORGANISM: streptococcus pyogenes

<400> SEQUENCE: 37

```
gatagaatgt ttctcactac tgttttagag ctaggccaac atgaggatca cccatgtctg   60
cagggcctag caagttaaaa taaggctagt ccgttatcaa cttggccaac atgaggatca  120
cccatgtctg cagggccaag tggcaccgag tcggtgcttt tt                     162
```

<210> SEQ ID NO 38
<211> LENGTH: 161
<212> TYPE: RNA
<213> ORGANISM: streptococcus pyogenes

<400> SEQUENCE: 38

```
gtgattataa agaaattgaa gttttagagc taggccaaca tgaggatcac ccatgtctgc   60
agggcctagc aagttaaaat aaggctagtc cgttatcaac ttggccaaca tgaggatcac  120
ccatgtctgc agggccaagt ggcaccgagt cggtgctttt t                      161
```

<210> SEQ ID NO 39
<211> LENGTH: 1810
<212> TYPE: RNA
<213> ORGANISM: streptococcus pyogenes

<400> SEQUENCE: 39

```
attaaggtcg ggcaggaaga gggcctattt cccatgattc cttcatattt gcatatacga   60
tacaaggctg ttagagagat aattagaatt aatttgactg taaacacaaa gatattagta  120
caaaatacgt gacgtagaaa gtaataattt cttgggtagt ttgcagtttt aaaattatgt  180
tttaaaatgg actatcatat gcttaccgta acttgaaagt atttcgattt cttggcttta  240
tatatcttgt ggaaaggacg aaacaccgca ttagggaatg gactgctgtt ttagagctag  300
gccaacatga ggatcaccca tgtctgcagg gcctagcaag ttaaaataag gctagtccgt  360
tatcaacttg gccaacatga ggatcaccca tgtctgcagg gccaagtggc accgagtcgg  420
tgcttttttc tagtaggtac cacgttgcaa cacgagttcg ctaaggtcgg gcaggaagag  480
ggcctatttc ccatgattcc ttcatatttg catatacgat acaaggctgt tagagagata  540
attgaatta atttgactgt aaacacaaag atattagtac aaaatacgtg acgtagaaag  600
taataatttc ttgggtagtt tgcagttttta aaattatgtt ttaaaatgga ctatcatatg  660
cttaccgtaa cttgaaagta tttcgatttc ttggctttat atatcttgtg gaaaggacga  720
aacaccgaca ggcagggaac aaggccagtt ttagagctag gccaacatga ggatcaccca  780
```

```
tgtctgcagg gcctagcaag ttaaaataag gctagtccgt tatcaacttg gccaacatga    840
ggatcaccca tgtctgcagg gccaagtggc accgagtcgg tgctttttc tataggtgaa    900 ttcaccgacg gtcgagccaa ctcaaggtcg ggcaggaaga gggcctattt cccatgattc    960
cttcatattt gcatatacga tacaaggctg ttagagagat aattagaatt aatttgactg   1020
taaacacaaa gatattagta caaaatacgt gacgtagaaa gtaataattt cttgggtagt   1080
ttgcagtttt aaaattatgt tttaaaatgg actatcatat gcttaccgta acttgaaagt   1140
atttcgattt cttggcttta tatatcttgt ggaaaggacg aaacaccgct tatgaaaagc   1200
cccagggcgt tttagagcta ggccaacatg aggatcaccc atgtctgcag ggcctagcaa   1260
gttaaaataa ggctagtccg ttatcaactt ggccaacatg aggatcaccc atgtctgcag   1320
ggccaagtgg caccgagtcg gtgctttttt ctagtagaag cttgtacaac gtcaaggctt   1380
cctaaggtcg ggcaggaaga gggcctattt cccatgattc cttcatattt gcatatacga   1440
tacaaggctg ttagagagat aattagaatt aatttgactg taaacacaaa gatattagta   1500
caaaatacgt gacgtagaaa gtaataattt cttgggtagt ttgcagtttt aaaattatgt   1560
tttaaaatgg actatcatat gcttaccgta acttgaaagt atttcgattt cttggcttta   1620
tatatcttgt ggaaaggacg aaacaccgca aacctctcca cctgctccgt tttagagcta   1680
ggccaacatg aggatcaccc atgtctgcag ggcctagcaa gttaaaataa ggctagtccg   1740
ttatcaactt ggccaacatg aggatcaccc atgtctgcag ggccaagtgg caccgagtcg   1800
gtgcttttt                                                           1810
```